(12) United States Patent
Keeling et al.

(10) Patent No.: US 6,881,433 B1
(45) Date of Patent: Apr. 19, 2005

(54) FOOD PRODUCTS CONTAINING ALTERED STARCH

(76) Inventors: Peter Lewis Keeling, 3409 Oakland St., Ames, IA (US) 50014; Ming-Tang Chang, 1419 Illinois Ave., Ames, IA (US) 50014-3760

( * ) Notice: Subject to any disclaimer, the term of this patent is extended or adjusted under 35 U.S.C. 154(b) by 0 days.

(21) Appl. No.: 09/118,990

(22) Filed: Jul. 20, 1998

Related U.S. Application Data

(63) Continuation of application No. 08/346,602, filed on Nov. 29, 1994, now abandoned, which is a continuation-in-part of application No. 08/263,921, filed on Jun. 21, 1994, now abandoned.

(51) Int. Cl.$^7$ ............................................. A23L 1/0522
(52) U.S. Cl. ...................................... 426/661; 426/578
(58) Field of Search ................................ 426/549, 622, 426/573, 578, 661; 127/32

(56) References Cited

U.S. PATENT DOCUMENTS

| | | | |
|---|---|---|---|
| 4,428,972 A | 1/1984 | Wurzburg et al. | |
| 4,767,849 A | 8/1988 | Friedman et al. | |
| 4,770,710 A | 9/1988 | Friedman | |
| 4,774,328 A | 9/1988 | Friedman et al. | |
| 4,789,557 A | 12/1988 | Friedman et al. | |
| 4,789,738 A | 12/1988 | Friedman et al. | |
| 4,790,997 A | 12/1988 | Friedman et al. | |
| 4,792,458 A | 12/1988 | Friedman et al. | |
| 4,798,735 A | 1/1989 | Friedman et al. | |
| 4,801,470 A | 1/1989 | Friedman et al. | |
| 5,004,864 A | 4/1991 | Robertson et al. | 800/235 |
| 5,034,323 A | 7/1991 | Jorgensen et al. | |
| 5,349,123 A | 9/1994 | Shewmaker et al. | 800/205 |
| 5,453,566 A | 9/1995 | Shewmaker et al. | |
| 5,516,939 A | 5/1996 | Pearlstein et al. | 536/102 |
| 5,824,790 A | 10/1998 | Keeling et al. | |
| 6,218,155 B1 | 4/2001 | Keeling et al. | |
| 6,274,792 B1 | 8/2001 | Keeling et al. | |

FOREIGN PATENT DOCUMENTS

| | | |
|---|---|---|
| WO | 94/22291 | 10/1994 |
| WO | 94/24264 | 10/1994 |

OTHER PUBLICATIONS

Neyra, Carlos A., "Biochemical Basis of Plant Breeding," vol. 1, Carbon Metabolism, Chapter 8, Synthesis and Breakdown of Starch (CRC Press, 1985), pp. 130–143.

Baba et al., Plant Physiology, vol. 102 (1993), pp. 565–573.

Murai et al., "Phasecolin Gene from Bean is Expressed After Transfer to Sunflower Via Tumor–Inducing Plasmid Vectors," Science (Nov. 1983), pp. 476–481.

Boyer, "Synthesis and Breakdown of Starch," Biochemical Basis of Plant Breeding, vol. 1, Chapter 8, pp. 133–146 (Date N.A.).

Napoli, "Introduction of a Chimeric Chalcone Synthase Gene Into Petunia Results in Reversible Co–Suppression of Homologous Genes in Trans," The Plant Cell, vol. 2, pp. 279–289 (Date N.A.).

Van der Krol et al., "Inhibition of Flower Pigmentation by Antisense CHS Genes: Promotor and Minimal Sequence Requirements for the Antisense Effect," Plant Molecular Biolog. (1990), pp. 457–466.

Sprague (editor): Corn and Corn Improvement, No. 18 in the Series Agronomy (1977).

Yamada, T., et al., "A Novel Type of Corn Starch From a Strain of Maize," Starch, vol. 30 (Sep.–Oct., 1974), pp. 145–148.

Yamada, T. et al. "A Novel Type of Corn Starch from a Strain of Maize" Starch, pp. 145–148, vol. 30 (9–10/1974).

Holder, D.G. et al., "Interaction of Shrunken 2 and Sugary 1 In Dosage Series In Corn Endosperm", Crop Science, pp. 647–648, vol. 14 (May 1978).

Boyer et al. "Interaction of the amylose–extender and waxy mutants of maize" The Journal of Heredity 67:209–214, 1976.

Murai et al. (1986) Phaseolin Gene from bean is expressed after Transfer to Sunflower via Tumor–Inducing Plasmid Vectors. Science vol. 222, pp. 476–481.

Boyer et al. (1956) Biochemical Basis of Plant Breeding, Synthesis and breakdown of starch. vol. 1, chapter 8 pp. 139–146.

Mrthy et al. (1986) Hulless barley selections combined with improved protein content and grain filling. Biological Abstrats 81(a)139.

*Primary Examiner*—Keith Hendricks
(74) *Attorney, Agent, or Firm*—Nixon & Vanderhye, P.C.

(57) ABSTRACT

Novel plants having an altered ability to produce starch, including an improved ability to produce structurally-altered starch or starch of altered quality are disclosed. The invention further relates to processes for obtaining such plants, wherein mutant plants are intercrossed to affect starch biosynthesis.

43 Claims, 16 Drawing Sheets

FIG. 1

E coli glycogen synthase (SEQ ID NO:1)

```
gtgattggtgaaaacgcagaggaagagatgcagtcgtttctatcgttcagagaaggcatcgtgctgtaa
cgcgcgaaatgctacggagaagttagggcggcataaacaggagcgatatgcaggtttacccgcagttcagag
atgttccgctgcttaaaaaccgctactcgcgtactccgcattcgcattcgcattcgcattgccgatcgcagg
acggcgttgacgtcgacttgcgcgtgatacctcgcgcgacatatcgcgttgttcggtcattacaacggggttggcatt
agtatccgtcgattgacaacgtattgcgtctttgcgcatgttcggggtggcaacctgccagcggcttgtcc
taccctgatcgatcaacgtcctgattggtcgtgaagtccgggtgggcatgggcagaaaggcctgcatcgccggcg
atctctggcgcgtgaagtatgacatccaatcgtcgtcatggtctgccctactatacgcggaattcggaatccaaacgctcgcacatctc
ccgggcgccgagtcgtttgccctactgtactacgacagcggaagggcctcgtgcgttacac
acatgaatgacatcaacgccgtttgcctactactgtactacgacgagagaaatctgagttccagagcgccagtcacaatctgagttcgttgac
tttcctgaaccgcagttgccgaagcgcctactactgtactactactgagaagcgagtcacaatcgcactccaaggttgac
accgcagatcgttggaagatcggaagatacggaaaataaagcgatcactgatcacaatcgcaagcaggtctcgattcgggtgctggaag
ccgtcgtcgatacgtccgctttttgcagtggtgagcgcttttttgcagtggtgagcgtttactgccggttttactgcaag
gataaagtgccgctttttgcagtagttttcaggaaacgcctacatgaatgaatgctctccccgtttacatcatcgcccacgctt
ccctcaccgggttcttccggagcagcgcggcagctgccgcgctactcggcgatccggtgtgctgcagga
aggttccttgcggcgcggcagcggaatacccggttcagttgctatcacgaagcattt
tcgcatcgcattatgggcgcggacgtcattctggtgccccagcgtttcgaaccgtggcttaacgc
aactttatcgttcctcgagaacgcttcgagatgctcgccaatggcgtcgccaatggggtttatctgaagatagtaatgcctgg
tgactgttcctcgagaacgcttcgagatgctcgcaatggcgtcgccatgtcctgtcctccactgtggcggttgcaac
tcgctgttacggacttatcggatgcaatggcttttggcttggttggcgtttactgaatccgtaccgtgagctttactatcgctc
gtcaggctatgtttcaggaatgcctacatgaatgaatgctctccccgtttacatcatcgcccacgctt
gaaatagtttcaggaaacgcctacatgaatgaatgctctccccgtttacatcatcgcccacgctt
```

FIG. 2

A) WL : AGA.1 (SEQ ID NOS: 2-3)

FIG. 3 (1/2)

B) WE: AGA3 (SEQ ID NOS: 4-5)

```
  E  L  V  Q  K  H  V  D  D  N  A  D  I  T  L  S  C  A  P  V  G  E  S  R  A  S  E  Y  G  L  V  K  F  D  S  S  G  R  V  V
CGAGCTTGTGCAGAAACATGTGGATGACAATGCTGACATTACTTTATCATGTGCCCCTGTTGGAGAGAGCCGGAGCCTAGTGAAGTTCGACAGTTCAGGCGTGTGG
          10        20        30        40        50        60        70        80        90       100       110       120

Q  F  S  E  K  P  K  G  D  D  L  E  A  H  K  V  D  T  S  F  L  N  F  A  I  D  D  P  A  K  Y  P  Y  I  A  S  H  G  V  Y
TCCAATTTTCTGAGAAGCCAAAGGGTGACGATCTGGAAGCTCATAAAGTTGATACCAGTTTTCTCAATTTCGCCATCGACGACCCTGCTAAATATCCATATATTGCTTCTCATGGGAGTCT
         130       140       150       160       170       180       190       200       210       220       230       240

V  F  K  R  D  V  L  L  N  L  L  K  S  R  Y  A  E  L  H  Q  F  G  S  E  I  L  P  R  A  L  H  D  H  N  V  Q  A  Y  V  F
ATGTGTTCAAAAGAGATGTTCTTCTAAACTTGCTCAAGAGTCAAGATACGCAGAGCTACATGACATTTGGGTCTGAAATCCTCCCGAGAGCTCTGCATGACCACAATGTACAGGCTTATGTCT
         250       260       270       280       290       300       310       320       330       340       350       360

T  D  Y  H  E  D  I  G  T  I  A  R  S  F  F  D  A  N  H  S  L  C  E  Q  P  P  K  F  E  F  Y  D  P  K  T  P  F  F  T  S  P
TCACTGACTACCATGGAGGACATCGGAACAATCAGATCCTTCTTCGATGCGAACCACAGCCTCCTGTGAAGCAGCCCCCAAAGTTCGAGTTTTATGATCCCAAAACTCCCTTCTTCACTCC
         370       380       390       400       410       420       430       440       450       460       470       480
```

```
              R Y L P P T K S Q K C R I K E A I I L H G C F L R E C K I E H S I I G V P S R L
CTCGATACTTGCCACCAACAAGTCAGACAATGTGCAGGATCAAAGAAGCGATCATTCTTCATGGCTGCTTCTTGCGTGAATGAAAATCGAGACTTCCATCATCGGCGTTCTTCAGGCC
       490       500       510       520       530       540       550       560       570       580       590       600

N S G S E L K N A H H H G A D S Y E T E Q E I S R L H S E G K V P I G V G E N T
TAAACTCCGGGAGCTGAAGAACGCGGATCATCATCATGGAGCGGATTCGTACGAGACAGAGCAGGAGATCAGCAGGCTTCATGTCGAGGGCAAGGTCCCCATCGGCGTCGGGGAGAACA
       610       620       630       640       650       660       670       680       690       700       710       720

K I S N C I I D H N A R I G R D V V I S N K E G V Q E A D R P E E G Y Y I R S G
CAAAGATCAGCAACTGTATCATCGATCATAACGCGCGCATCGGCCGAGACGTGGTCATCTCAAACAAGGAGGGCGTGCAAGAGGCCGACAGGCCCGAAGAGGGCTACTACATCAGGTCCG
       730       740       750       760       770       780       790       800       810       820       830       840

I V V I Q K N A T I K D G T V V
GGATCGTCGTGATCCAGAAGAACGCGACCATCAAGGACGGCACCGTCGTCAGTACCGGGGTCGGCGTCGACGGGTTCTCGCGACAACCTTCTCCGTCGTCGATCGTCGTCGTCTCGAG
       850       860       870       880       890       900       910       920       930       940       950       960

GCCGGGAGGACTGAAGGAGCGGAGGGACGGGCAGCGCGCCGGCGAGCATTAGTAGCCGAGAATGACTGAATGACTTGAATGACTTGAAGCTTGAATGACTGAAGCAAGTAA
       970       980       990      1000      1010      1020      1030      1040      1050      1060      1070      1080

TAGTCGTTCGTTTTCCCTGTAATAAATAAGAGGCTGTCGTGTTGAGTAAAGAGTGGCAGCGAGCAAAACTCCGGGGATGTTCGTGTAAATAAAACTCTATCTAGACCTGTGA
      1090      1100      1110      1120      1130      1140      1150      1160      1170      1180      1190      1200

AATTTTCAAAAAAAAAAAAAAAAAAAAAAAAAAAAAAAAAAAAAAAAAAAAAAAAAAAAAAAAAAAAAAAAA
      1210      1220      1230      1240      1250      1260      1270
```

C) WE : AGA.7 (SEQ ID NOS: 6-7)

```
   R  A  S  P  P  S  E  S  R  A  P  L  R  A  P  Q  R  S  A  T  R  Q  H  Q  A  R  Q  G  P  R  K  C  N  G  G  R  G  P  P
CGTGCGCTTCTCCCCGTCAGAGTCTGAGGGCTCCTGCAGCCCGCGCCTCAAAGGTCGGCCGACGCAGCATCAGGGCGACGGGGTCCCAGGAGGATGTGCAAGGCGGAGGGCGCGGCCCGGA
              10          20          30          40          50          60          70          80          90          100         110         120

Y  W  T  A  G  V  T  S  A  P  A  R  Q  T  P  L  F  S  G  R  P  S  G  G  L  S  Q  P  N  E  V  A  A  V  I  L  G  G  G  T
TACTGGACAGCTGGTGTCACTTCCGCCCCAGCCCGGCAGACCCCGGACCCCTCTTCTCCGGAAGATTAAGCGATCCTCAGGAGAACGAGGTTGCCGCCGTCATACTCGGCGGCGGCACC
              130         140         150         160         170         180         190         200         210         220         230         240

G  T  Q  L  F  P  L  T  S  T  R  A  T  P  A  V  P  I  G  G  C  Y  R  L  I  D  I  P  H  S  N  C  F  N  S  G  I  N  K  I
GGGACTCAGCTCTTCCCACTCACGAGCACGAGGGCCACACCTGCTGTTCCTATTGGAGGATGCTATAGACTGATTGACATCCCACATAGCAACTGCTTCAACAGTGGCATCAACAAGATA
              250         260         270         280         290         300         310         320         330         340         350         360

F  V  H  T  Q  F  N  S  A  S  L  N  R  H  I  H  R  T  Y  L  G  G  I  N  F  T  Q  G  S  V  E  V  L  A  A  T  Q  H  P
TTCGTTCATGACCCAGTTCAACTCGGCCTCCCTTAATCGTCATTAATCGCCACACTTACCTGGGCGGGGGGAATCAATTTCACTCAGGATGGATCCGTTGAGGTATTGGCCGCGACAGCAAATCCCC
              370         380         390         400         410         420         430         440         450         460         470         480

G  E  A  A  G  H  F  R  G  T  A  D  A  W  R  K  I  I  W  V  L  E  D  Y  Y  K  N  K  S  I  E  H  I  L  I  L  S  G  D  Q
GGGGAAGCGCTGCTGGCTGGATGGTTCCGCGGAACAGGCCACCGCGTGGGAGAAAATTATCTGAGACTACTATCGCTGAGGACTACTATTATAAGAATAAATCGATAGAGCACATTTGATCTTGTCGGCGATCAG
              490         500         510         520         530         540         550         560         570         580         590         600
```

FIG. 4 (2/3)

```
L Y R H D Y H E L V Q K H V D D N A D I T L S C A P V G E S R A S E Y G L V K F
CTTTATCGCATGGATTACATGGAGCTTGTGCAGAAACATGTGGATGATAATGCAGATATTACTTTATCTGCACCTGTTGGGGAGAGCCGGGCATCTGAGTACGGGCTTAGTGAAGTTC
610       620       630       640       650       660       670       680       690       700       710       720

Q S S G R V V Q F S E Q P K G D D L E A H K V Q T S F L N F A I D D P A K Y P Y
CAGAGTTCAAGGCCGTGTGGTTCAGTTCGAGCAGCCTAAAGGGTGACGATCTGGAAGCACATAAAGTTCAAACCAGTTTCCTCAATTTCGCAATCGACGATCCTGCTAAATATCCATAC
730       740       750       760       770       780       790       800       810       820       830       840

I A S M G V Y V F K R D V L N L L K S R Y A E L H D F G S E I L P R A L H D H
ATTGCTTCAATGGGAGTCTATGTCTTCAAAAGAGATGTGCTTAATCTTCTCAAGTCTAGATATGCAGAACTACATGATTTTGGGTCTGAGATCCTCCCGAGAGCTCTTCATGACCAC
850       860       870       880       890       900       910       920       930       940       950

N V Q A Y V F T D Y H E D I G T I R S F F D A N R A L C E Q P P K F E F Y D P K
AATGTACAGGCTTATGTCTTCACTGACTACCATGAAGACATTGGAACAATCAGATCCTTCTTTGACGCAAACCGAGCCCTCTGCGAGCAGCCCCCAAAGTTCGAGTTTTATGATCCCAAA
970       980       990       1000       1010       1020       1030       1040       1050       1060       1070       1080

T P F F T S P R Y L P P T K S D K C R I K E A I L H G C F L R E C K I E H T A
ACTCCCTTCTTCACCTCGCCTCGGTATCTGCCACCAACAAAGTCAGACAAGTGCAGGATCATTCTGGAACGGCTGCTTCTTCGTGAATGCAAAATCGAGCACACTGCG
1090       1100       1110       1120       1130       1140       1150       1160       1170       1180       1190       1200
```

F S R L N S G S E L K H A H H H G A D S Y E T E D E H S R L M S E G K V P I G V
TTCTCACGGTCAAAACTCCGGAAGCCGAGCTCAAGCATGCACATCATCATGGCGCAGATTCGTACGAGACCGAAGACGAGATGTCGAAGGGCAAGGTCCCGATCGGCGTC
1210      1220      1230      1240      1250      1260      1270      1280      1290      1300      1310      1320

G E N T K I S N C I I D H N A R I G R D V V I S N K E G V Q E A D R P E E G Y Y
GGGGAGAACACAAAGATCAGCAACTGCATCATCGACCATAACGCCAGGATAGGGAAGGGACGTCATCTCAAACAAGAGGAAGGAGTGCAAGAACCGACACAGGCCGGAGGAGGGGTACTAC
1330      1340      1350      1360      1370      1380      1390      1400      1410      1420      1430      1440

I R S G I V V I Q K H A T I K D G T V V
ATCAGAGTCGGGATCGTGGTGATCCAGAAGAACGCGACCATCAAGGACGGCACCGTCGTGTAGTACCCGGGCCGGCCGGACGGGGTCCGGCGACAACTTCTCTGCGTGATCGTCGTCGT
1450      1460      1470      1480      1490      1500      1510      1520      1530      1540      1550      1560

CGGCTTCTCGGGGGCCGGGACTGAGGAGTGACCCGGGACGGGGGCGTTTGAAGCTTTGAATGGCTGAGACTGAAAGTGGAAGCCCGGAGGCCCAGGCCAGGCATCAGTAAGTAGTAAGTGGT
1570      1580      1590      1600      1610      1620      1630      1640      1650      1660      1670      1680

AGTAGGCAGTGGAAACAAAAGTAATAGTCGTTCGTTTTGCCCCTGTTAATAAATAAGAGAGGCTGTGTGTTGAGGTAAAGAAGAGTGGCCGCGGCAGCAAACAAAAAAAAAAAAAAAAAAAA
1690      1700      1710      1720      1730      1740      1750      1760      1770      1780      1790

```
gaattccaaatatatgatgattgttgtcctagtgcagaagaactaaatatactagcgaaaaaaaccttc
ctagtcatgtaagtgtatgggcatatagaaaaataaacatctccaagactccaaactagtcatagctttta
gtcacaacttcaaacacttcatgccaacagatcatggatttttttttgcctaagacaaaactagaat
gagaaaagaactaactcatcatacatattagtgcatcaaaaaatgacacatatgatACTAT
ATCACACAGGCCTTCAGTTTCTAGAACAAGTGCAGATCGAtgtgtgggtatgcatgtctaatattttact
aggttggatatgcatgggcgttcattcagaatcagttcacacagtttatcgcacttctgtttacaaaac
atggatttcattgctctgtactggctacatgcgtaaggatcaacttgtctaatctcaggtgcatcctcctt
gtcaagcaaacttaacaatttgataaaaaatgcagctttatatgtgaacccataacttaataattg
caggaaaactgatgtgcaaacaaaccaaatatactgcagagaaaactcctagtcatgtaagtgtATGGACATAT
tcaccatagtgcaaaagaaccaaatatactgcagagaaaactcctagtcatgtaagtgtATGGACATAT
AGAAATAAAACATCTCAAGACTCCAATAACAGGCTCAAGCTAACTAGTCATGGTGTGTTTTTTTTCCTAGGAA
GCAAACTAGTCACAACTTTAAACATTTCATGCCAGCATACATATCAGGATGATCATCAGGATTGATCTGTATAGACACGTATATGATA
AAGCTAGAATGAGAAAAGACCTAACTCAGCATACATATCAGGATAGTATCGTATAGACACGTATATGATA
CTATATCACGCCAGCCGTTCAATTTCTAGAACAAATGCAGATTGATCTGTGAATATGCATGTCTCATATTT
TACTAGGTTGGACTGAATCCCGTGAAACAAACAATTTATTCAACAAgttctgcatgaatatcatc
tcaaattcaataatcactctcgttgataaaaaaatgcaaccaacagttaaccagaagtgaaaatagaaac
tatttgaatcagatcactccgttattcacatacacagtaacaagaactagaattgagcatgtgagtATT
attgtttaccatcaatttcaagtacacagtaacaagaactagaattgagcatgtgagtATT
GTTGATACCTCGTTGAGCTCTCTCTGCCCGGCTTTCTGCTCGGCagcaagagccagctcagatccacc
ccgaaagcttgggcgtaggtgttgtctatcgcgaaaacacgcgcggtacgccaagacagcgcggccat
```

FIG. 5 (2/3)

```
ctccatcccaggcacggtgcgcccgcttttcgccgtctcgctgagtcacggcgggcgtccagcaggtag
ttgagcgccttccgcggcacgaatcgctgcgtgcgggcccGGATCTGGTCGAGTTGGTAGTCAGCGTCGGT
GTCGAATGCCGGGACGTCgaccaggaagaagttgccgtcgctgtggtggggacgaaggcgtcaggattg
tcgcaagggcagagcccagcCCTGGGcggGGGCCGCCTTCTCGGTGAAGTGGtCCtcgaagggacgagctcgtgggg
GcTGCGGGAcgTGCccgTGCccgCCTGGGcggGGGCCGCCTTCTCGGTGAAGTGGtCCtcgaagggacgagctcgtgggg
tcaaaccaccccatagctcGAGTCACCGGAAGAAGGCGACGAGGACGAGCCCGTCgcGGTGGCCgcgGTGT
ACCTCCTCGTCGTCGGTGAggctGACGCTGTAGATATGGCCAGGCCACACGGATGGGACTTCACCTTGG
CCCAGACCATGTCGCCGAACCGGGGCCGCcgTTCGCCCATGCCGTTCCGGAGGGAAACCTAGATTTGGATGCAGGAACCAT
GGCGCCTCCAGCGCGGCGGGTCGGACATCCTGTGGAGGGGTGGCCTGGGATCGGTGAACGATGACTATATTCTTCTCTCGGGGACT
ATTGGTCTGGGCTTGGGTTCCGGAGAAATTCGAGAGACTAATATTTATCTTATCAAGTTTATATTCTTCTCTCGGGGACT
GTAATTTTATTATTATAAATAGTATTTTATCAAGTTGGCTAATCTGTGTAATGATCATATCATATCTACATATCTACTAT
ATGTAGTATAAAGtgtAAAATAAGTATTTTATCAAGTCTAGGCTATCTGTGTAATGATCATATCATATCATATCATATCTACTAT
GTGGAGTTGTTTTGGCGGCTACATAATTCTTAGGCTAATCTGTGTAATCATTTTACACGGTATGTTGT
CACATTCTCTATTTTAAATTTGTGCGACGGAGTTGGATAGAGATGGTGAACAGCTGGATAGATATATGATTATAGG
ACACAGCCCTATCGTGgcGGAcggGAGTTGGATAGAGATGGTGAACAGCTGGATAGATATATGATTATAGG
CGATTGGGTAGATGTGATTTGATAGGCTAGTGGTGTTAGGAGCGATTAGTGAGACATTGTAAATAATTAGG
TTGATGTGATCCGAGGATGGCTAGTGGTGTTAGGAGCGATTAGTGAGACATTGTAAATAATTAGG
CATTATATATGTTTAAATTCTAAGAAATTTGTTGTGTTAAATTGTTATCCACATAGATTATTAGCC
ATCTCAAAGAGAGGTTTGGGTTGTTACACAAATATTCGTTTGCTTCTACATAGATTATATGTTTT
TATTTACAATGAAAACTATATTTTATTCATCTACTCACCCAGCACACAGAAATTCTGGTTGAGTAGATGAA
```

FIG. 5 (3/3)

```
AAAAACTACAACAAACTCTTCCTGAAAGTGTCGGTGTGAAGCCGAGAAATCCTTTCATTTCGGTGACG
GAGCCCCTTGCTGCTGCTGCTCAGTGCACTCCGTTCGCCTGCCACTACAAGCGACGGCCGACGAC
TCGCAAGTATCGGTAGGCATTTAAAACTGAAAACCTAAACCCGAATAGACCAAATTGTTGGTTT
ATTCGGGTTTTTGGGTTCGGATTCGGTTCTAAATATGCTATATTTTAGGGTATAGGTTCGGGTTCAGTT
TCTAACCTTTAAAACCTGAATAGACGAATAACCCGAAATAAAAATCTCTTAATATGTGATGATATTA
TTATATGATTTATGAACTTATTAACCGAAAATGATACCATCCTAACGATAGTATATATCTATGTA
TGCTATTTTTATAGTCACTTGTGTAATAATAGTACTTCCAATTAATAATCAGTGTATATATTTAACA
AAAGATACTAGCCCTCTCTACTATTTGAGTAGTATATTCGGTGCACCGAATAGACCGAAATTGTAAGTC
TATTCAGTTCGTTCGTTCCTAAAATATTTTAAAAATTTGGTTCTCATATTTCAGAATCCGAAATTCATA
AATCCAAATAGACCGAACAAATTaCGCTAATAGACCGAATAACTAGCGTACTCgCAAGTCGCACCCAC
TAGCCTGCTGCTGCTAAGCGAGGAgACTCCAAGAACCAGAACCAGCGCCAgCTCtAACGTCACCT
TAGCCACCTTCTTCCTCTCCAAGaCTCCCAATCCCCAACCACCAGCCGCCAgCTCtAACGTCACCT
CTGATTTCTCTCTCTCCTCTATTGCTAGCTGCTGTTTATTATAGTAGCAGCTGCAGCAGGAGCTGCA
CACACCCATCCAATTCCAGCTGCTGATCTTGATCCTGCACCCGAGCCGTACACAAGAGCTAGTCGGTAG
AAcTTGCAGGAGCGGAgCAGAACTAAGTGCAGAGAACAGGACATATG
                                              |
                                        translation start point
```

FIG.6(1/3)

```
          10         20         30         40         50
          |          |          |          |          |
  1 CCAGCTGCTG ATCTTGATCC TGCACCCCGA GCCGTACACA AGAGCTAGTC
    GGTCGACGAC TAGAACTAGG ACGTGGGGCT CGGCATGTGT TCTCGATCAG

51 GGTAGAACTT GCAGGAGCGG AGCAGAACTA AGTGCAGAGA ACAGGACATA
    CCATCTTGAA CGTCCTCGCC TCGTCTTGAT TCACGTCTCT TGTCCTGTAT

101 TGGCTACGCC GGCGGTGAAG GTTTACGGGT GGGCTATCTC GCCGTTCGTA
    ACCGATGCGG CCGCCACTTC CAAATGCCCA CCCGATAGAG CGGCAAGCAT

151 TCGCGGGCTC TGCTGGCCCT GGAGGAGGCC GGCGTCGACT ACGAGCTCGT
    AGCGCCCGAG ACGACCGGGA CCTCCTCCGG CCGCAGCTGA TGCTCGAGCA

201 CCCCATGAGC CGCCAGGACG GCGACCACCG CCGCCCCGAG CACCTCGCCA
    GGGGTACTCG GCGGTCCTGC CGCTGGTGGC GGCGGGGCTC GTGGAGCGGT

251 GGAACCCTTT CGGGAAGGTG CCGGTGCTCG AGGATGGCGA CCTCACGCTC
    CCTTGGGAAA GCCCTTCCAC GGCCACGAGC TCCTACCGCT GGAGTGCGAG

301 TTCGAATCAC GTGCGATCGC GAGGCATGTT CTCCGGAAGC ACAAGCCGGA
    AAGCTTAGTG CACGCTAGCG CTCCGTACAA GAGGCCTTCG TGTTCGGCCT

351 GCTGCTGGGC GGCCAGGC TGGAGCAGAC GGCGATGGTG GACGTGTGGC
    CGACGACCCG CCGGTCCG ACCTCGTCTG CCGCTACCAC CTGCACACCG

401 TGGAGGTGGA GGCCACCAG CTGAGCCCGC CGGCGATCGC CATCGTGGTG
    ACCTCCACCT CCGGTGGTC GACTCGGGCG GCCGCTAGCG GTAGCACCAC
```

FIG. 6 (2/3)

```
401 TGGAGGTGGA GGCCCACCAG CTGAGCCCGC CGGCGATCGC CATCGTGGTG
    ACCTCCACCT CCGGGTGGTC GACTCGGGCG GCCGCTAGCG GTAGCACCAC

451 GAGTGCGTGT TCGCGCCGTT CCTGGGCCGC GAGCGCAACC AGGCGGGTGGT
    CTCACGCACA AGCGCGGCAA GGACCCGGCG CTCGCGTTGG TCCGCCACCA

501 GGACGAGAAC GTGGAGAAGC TCAAGAAGGT GCTGGAGGTG TACGAGGCGC
    CCTGCTCTTG CACCTCTTCG AGTTCTTCCA CGACCTCCAC ATGCTCCGCG

551 GGCTGGCCAC GTGCACGTAC CTCGCCCGCG ACTTCCTCAG CCTCGCCGAC
    CCGACCGGTG CACGTGCATG GAGCGGGCGC TGAAGGAGTC GGAGCGGCTG

601 CTCAGCCCCT TCACCATCAT GCACTGCCTC ATGGCCACCG AGTACGCCGC
    GAGTCGGGGA AGTGGTAGTA CGTGACGGAG TACCGGTGGC TCATGCGGCG

651 TCTCGTCCAT CGGCTCCCGC ACGTCAGCGC CTGGTGGCAG GGCCTCGCCG
    AGAGCAGGTA GCCGAGGGCG TGCAGTCGCG GACCACCGTC CCGGAGCGGC

701 CGCGCCCGGC GGCCAACAAG GTGGCGCAGT TCATGCCGGT CGGCGCCGGA
    GCGCGGGCCG CCGGTTGTTC CACCGCGTCA AGTACGGGCCA GCCGCGGCCT

751 GCGCCCAAGG AACAGGAGTG ACGATGAAGC GATCGAAGCG ACTTGTGTTG
    CGCGGGTTCC TTGTCCTCAC TGCTACTTCG CTAGCTTCGC TGAACACAAC
```

```
801  TTGTGCTTGA TTAGTTAATT GGAAACCTTC TCACTCATCT AGTCCATCAT
     AACACGAACT AATCAATTAA CCTTTGGAAG AGTGAGTAGA TCAGGTAGTA

851  GGTGCCTGCT TTTCTTTATA CTATTTGTCT TAATTTTGCT GCTTCTCCA
     CCACGGACGA AAAGAAATAT GATAAACAGA ATTAAAACGA CGAAAGAGGT

901  CGGAATAATA GTAGAGATTT GGAAATGTAA TGTATTTATC AAAAAAAAA
     GCCTTATTAT CATCTCTAAA CCTTTACATT ACATAAATAG TTTTTTTTT

951  AAAA
     TTTT
```

FIG. 6 (3/3)

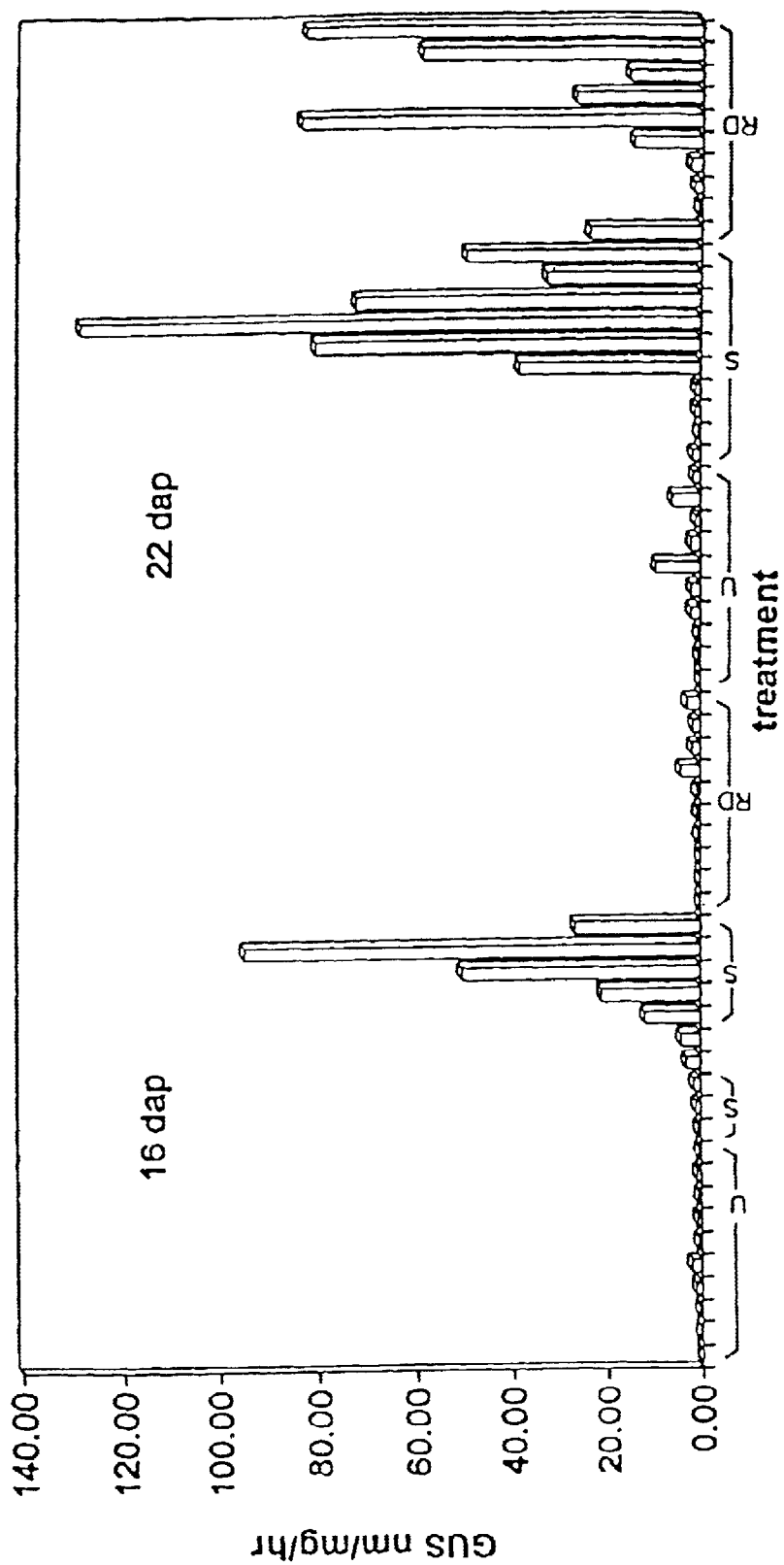
FIG. 9 GUS activity in endosperm after safener root drench/spray

SEQUENCE LISTING (1) GENERAL INFORMATION:

(iii) NUMBER OF SEQUENCES: 43

(2) INFORMATION FOR SEQ ID NO: 1:

(i) SEQUENCE CHARACTERISTICS:
      (A) LENGTH: 1601 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
    (A) ORGANISM: FIGURE 1 E COLI GLYCOGEN SYNTHASE (xi) SEQUENCE DESCRIPTION: SEQ ID NO: 1:

```
GTGATTGGTG AAAACGCAGA GGAAGATGCA CGTCGTTTCT ATCGTTCAGA AGAAGGCATC      60
GTGCTGGTAA CGCGCGAAAT GCTACGGAAG TTAGGGCATA ACAGGAGCG  ATAATGCAGG     120
TTTTACATGT ATGTTCAGAG ATGTTCCCGC TGCTTAAAAC CGGCGGTCTG GCTGATGTTA    180
TTGGGGCATT ACCCGCAGCA CAAATCGCAG ACGGCGTTGA CGCTCGCGTA CTGTTGCCTG    240
CATTTCCCGA CATTCGCCGT GGCGTGACCG ATGCGCAGGT AGTATCCCGT CGTGATACCT    300
CCGCCGGACA TATCACGCTG TTGTTCGGTC ATTACAACGG GGTTGGCATT TACCTGATTG    360
ACGCGCCGCA TCTCTATGAT CGTCCGGGAA GTCCGTATCA CGATACCAAC TTATTTGTCC    420
ATACCGACAA CGTATTGCGT TTTGCGCTGC TGGGGTGGGT TGGGGCAGAA ATGGCCAGCG    480
GGCTTGACCC ATTCTGGCGT CCTGATGTGG TGCATGCGCA CGACTGGCAT GCAGGCCTTG    540
CGCCTGCGTA TCTGGCGGCG CGCGGGCGTC CGGCGAAGTC GGTGTTTACT GTGCACAACC    600
TAGCCTATCA AGGCATGTTT TATGCACATC ACATGAATGA CATCCAATTG CCATGGTCAT    660
TCTTTAATAT TCATGGGCTG GAATTCAACG GACAAATCTC TTTCCTGAAG GCCGGTCTGT    720
ACTATGCCGA TCACATTACG GCGGTCAGTC CAACCTACGC TCGCGAGATC ACCGAACCGC    780
AGTTTGCCTA CGGTATGGAA GGTCTGTTGC AACAGCGTCA CCGCGAAGGG CGTCTTTCCG    840
GCGTACCGAA CGGCGTGGAC GAGAAAATCT GGAGTCCAGA GACGGACTTA CTGTTGGCCT    900
CGCGTTACAC CCGCGATACG TTGGAAGATA AAGCGGAAAA TAAGCGCCAG TCACAAATCG    960
CAATGGGATC CAAGGTTGAC GATAAAGTGC CGCTTTTTGC AGTGGTGAGC CGTCTGACCA   1020
GCCAGAAAGG TCTCGATTCG GTGCTGGAAG CCTCACCGGG TTCTTCGGAG CAGGGCGGGC   1080
AGCTGGCGCT ACTCGGCGCG GGCGATCCGG TGCTGCAGGA AGGTTTCCTT GCGGCGGCAG   1140
CGGAATACCC CGGTCAGGTG GGCGTTCAGA TTGGCTATCA CGAAGCATTT TCGCATCGCA   1200
TTATGGGCGG CGCGGACGTC ATTCTGGTGC CCAGCCGTTT CGAACCGTGC GGCTTAACGC   1260
AACTTTATGG ATCGAAGTAC GGTACGCTGC CGTTAGTGCG ACGCACCGGT GGGCTTGCTG   1320
ATACGGTTTC TGACTGTTCT CTCGAGAACC TTGCAGATGG CGTCGCCAAT GGGTTTATCT   1380
TCGAAGATAG TAATGCCTGG TCGCTGTTAC GGACTATTCG ACGTGCTTTT GTACTGTGGT   1440
CCTGTCCTCC ACTGTGGCGG TTTGTGCAAC GTCAGGCTAT GGCAATGGAT TTTGGCTGGC   1500
AGGTCGCGGC GAAGTCGTAC CGTGAGCTTT ACTATCGCTC GAAATAGTTT TCAGGAAACG   1560
CCTACATGAA TGCTCCGTTT ACATATTCAT CGCCCACGCT T                       1601
```

(2) INFORMATION FOR SEQ ID NO: 2:

(i) SEQUENCE CHARACTERISTICS:
        (A) LENGTH: 947 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: FIGURE 2 WL.AGA.1

(xi) SEQUENCE DESCRIPTION: SEQ ID NO: 2:

```
GGGGTGCTGA TTCTTTCTGG CGATCACCTC TACCGTATGG ACTACATGGA TTTTGTTCAG      60
```

-continued

```
AGTCATCGGC AGAGAGACGC GGGGATCAGC ATCTGTTGCT TGCCTATTGA TGGCAGCCGG      120

GCGTCTGATT TTGGTCTCAT GAAGATAGAC GACACAGGAA GAGTTATTTC ATTTAGTGAA      180

AAACCGAGAG GAGCTGATTT AAAGGAAATG GAGGAAGCAG AAAAGAAACC ATACATAGCT      240

TCAATGGGAG TATACATATT CAAGAAAGAG ATACTTCTAA ATCTTTTGAG ATGGCGTTTT      300

CCCACTGCAA ATGATTTTGG ATCTGAAATA ATTCCAGCTG CAGCAAGAGA GATTAATGTA      360

AAGGCATATC TTTTCAATGA TTACTGGGAA GATATTGGAA CTATCAAATC CTTCTTCGAA      420

GCAAATCTTG CCCTTGCTGA ACAGCCTTCA AAGTTCAGCT TCTATGATGC TAGCAAACCG      480

ATGTACACAT CGCGAAGAAA CCTACCACCA TCTATGATCA GCGGTAGTAA GATCACTGAT      540

TCGATCATTT CCCATGGATG TTTCTTGGAT AAATGCAGGG TAGAGCACAG TGTCGTTGGA      600

ATCCGTTCTC GAATAGGCTC CAACGTACAC CTCAAGGATA CGGTAATGCT CGGTGCTGAT      660

TTCTATGAAA CTGACATGGA AAGAGGCGAC CAGCTGGCCG AAGGAAAGGT TCCGATTGGG      720

ATCGGGGAGA ACACTTCGAT TCAAAACTGC ATCATTGACA AGAATGCGAG GATAGGGAAG      780

AATGTGACCA TTGCTAACGC CGAGGGTGTA CAGGAAGCGG ACAGGGCGTC AGAAGGCTTC      840

CACATCCGGT CCGGTATCAC GGTTGTGCTG AAGAACTCGG TGATTGCGGA TGGATTAGTC      900

ATATGAGCTG AAAAAAGGCG GTTCTCCAGT CCAGCAAGAG AAATAAA                   947
```

(2) INFORMATION FOR SEQ ID NO: 3:

(i) SEQUENCE CHARACTERISTICS:
        (A) LENGTH: 301 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: FIGURE 2 WL.AGA.1

(xi) SEQUENCE DESCRIPTION: SEQ ID NO: 3:

```
Gly Val Leu Ile Leu Ser Gly Asp His Leu Tyr Arg Met Asp Tyr Met
1               5                   10                  15

Asp Phe Val Gln Ser His Arg Gln Arg Asp Ala Gly Ile Ser Ile Cys
            20                  25                  30

Cys Leu Pro Ile Asp Gly Ser Arg Ala Ser Asp Phe Gly Leu Met Lys
        35                  40                  45

Ile Asp Asp Thr Gly Arg Val Ile Ser Phe Ser Glu Lys Pro Arg Gly
    50                  55                  60

Ala Asp Leu Lys Glu Met Glu Glu Ala Glu Lys Lys Pro Tyr Ile Ala
65                  70                  75                  80

Ser Met Gly Val Tyr Ile Phe Lys Lys Glu Ile Leu Leu Asn Leu Leu
                85                  90                  95

Arg Trp Arg Phe Pro Thr Ala Asn Asp Phe Gly Ser Glu Ile Ile Pro
            100                 105                 110

Ala Ala Ala Arg Glu Ile Asn Val Lys Ala Tyr Leu Phe Asn Asp Tyr
        115                 120                 125

Trp Glu Asp Ile Gly Thr Ile Lys Ser Phe Phe Glu Ala Asn Leu Ala
    130                 135                 140

Leu Ala Glu Gln Pro Ser Lys Phe Ser Phe Tyr Asp Ala Ser Lys Pro
145                 150                 155                 160

Met Tyr Thr Ser Arg Arg Asn Leu Pro Pro Ser Met Ile Ser Gly Ser
                165                 170                 175
```

```
Lys Ile Thr Asp Ser Ile Ile Ser His Gly Cys Phe Leu Asp Lys Cys
            180                 185                 190

Arg Val Glu His Ser Val Val Gly Ile Arg Ser Arg Ile Gly Ser Asn
            195                 200                 205

Val His Leu Lys Asp Thr Val Met Leu Gly Ala Asp Phe Tyr Glu Thr
            210                 215                 220

Asp Met Glu Arg Gly Asp Gln Leu Ala Glu Gly Lys Val Pro Ile Gly
225                 230                 235                 240

Ile Gly Glu Asn Thr Ser Ile Gln Asn Cys Ile Ile Asp Lys Asn Ala
                245                 250                 255

Arg Ile Gly Lys Asn Val Thr Ile Ala Asn Ala Glu Gly Val Gln Glu
            260                 265                 270

Ala Asp Arg Ala Ser Glu Gly Phe His Ile Arg Ser Gly Ile Thr Val
            275                 280                 285

Val Leu Lys Asn Ser Val Ile Ala Asp Gly Leu Val Ile
    290                 295                 300
```

(2) INFORMATION FOR SEQ ID NO: 4:

(i) SEQUENCE CHARACTERISTICS:
        (A) LENGTH: 1250 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: FIGURE 3 WE.AGA.3

(xi) SEQUENCE DESCRIPTION: SEQ ID NO: 4:

```
CGGAGCTTGT GCAGAAACAT GTGGATGACA ATGCTGACAT TACTTTATCA TGTGCCCCTG      60
TTGGAGAGAG CCGGGCATCT GAGTACGGGC TAGTGAAGTT CGACAGTTCA GGCCGTGTGG     120
TCCAATTTTC TGAGAAGCCA AAGGGTGACG ATCTGGAAGC GATGAAAGTG GACACCAGTT     180
TTCTCAATTT CGCCATCGAC GACCCTGCTA AATATCCATA CATTGCTTCT ATGGGAGTCT     240
ATGTCTTCAA AGAGATGTT CTGCTCAACC TTCTAAAGTC AAGATACGCA GAACTACATG      300
ACTTTGGGTC TGAAATCCTC CCGAGAGCTC TGCATGACCA CAATGTACAG GCTTATGTCT     360
TCACTGACTA CTGGGAGGAC ATTGGAACAA TCAGATCCTT CTTCGATGCG AACATGTCCC     420
TCTGCGAGCA GCCCCCAAAG TTCGAGTTTT ATGATCCCAA AACTCCCTTC TTCACCTCGC     480
CTCGATACTT GCCACCAACA AAGTCAGACA AGTGCAGGAT CAAAGAAGCG ATCATTCTGC     540
ACGGCTGCTT CTTGCGTGAA TGCAAAATCG AGCACTCCAT CATCGGCGTT CCTTCACGCC     600
TAAACTCCGG AAGCGAACTC AAGAACGCGA TGATGATGGG TGCGGATTCG TACGAGACCG     660
AGGATGAGAT CTCGAGGCTG ATGTCCGAGG GCAAGGTCCC CATCGGCGTC GGGGAGAACA     720
CAAAGATCAG CAACTGCATC ATCGACATGA ACGCGAGGAT AGGAAGGGAC GTGGTCATCT     780
CAAACAAGGA GGGAGTGCAA GAAGCCGACA GGCCGGAGGA GGGGTACTAC ATCAGGTCCG     840
GGATCGTGGT GATCCAGAAG AACGCGACCA TCAAGGACGG CACCGTCGTG TAGTACCCGG     900
GTCGGCGTGA CGGGTTCTGC GACAACCTCT CGCTGCGTTG ATCGTCGTCG TCGTCTCGAG     960
GCCCGGGAGG GACTGAAGAA GTGACCGGGG ACGGGAGGCG TTTGAAGCTT GAATGACTGA    1020
GAAGGCGCGC GCGGGCAGCA TTAGTAGTAA GTAGTAGTAA GGAGCAGTGG AACAAAGTAA    1080
TAGTCGTTCG TTTTTCCCCT GTAATAAATA AGAGGCTGTG TGTTGAGGTA AAGAAGTGGC    1140
```

```
AGCGAGCAAA CAAACTCCCG GGGGATGTTC GTGTAAATAA AACTCTATCT AGACCTGTGA    1200

AATTTTCAAA AAAAAAAAAA AAAAAAAAAA AAAAAAAAAA AAAAAAAAAA              1250
```

(2) INFORMATION FOR SEQ ID NO: 5:

(i) SEQUENCE CHARACTERISTICS:
        (A) LENGTH: 296 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: FIGURE 3 WE.AGA.3

(xi) SEQUENCE DESCRIPTION: SEQ ID NO: 5:

```
Glu Leu Val Gln Lys His Val Asp Asp Asn Ala Asp Ile Thr Leu Ser
1               5                   10                  15

Cys Ala Pro Val Gly Glu Ser Arg Ala Ser Glu Tyr Gly Leu Val Lys
            20                  25                  30

Phe Asp Ser Ser Gly Arg Val Val Gln Phe Ser Glu Lys Pro Lys Gly
        35                  40                  45

Asp Asp Leu Glu Ala Met Lys Val Asp Thr Ser Phe Leu Asn Phe Ala
50                  55                  60

Ile Asp Asp Pro Ala Lys Tyr Pro Tyr Ile Ala Ser Met Gly Val Tyr
65                  70                  75                  80

Val Phe Lys Arg Asp Val Leu Leu Asn Leu Lys Ser Arg Tyr Ala
                85                  90                  95

Glu Leu His Asp Phe Gly Ser Glu Ile Leu Pro Arg Ala Leu His Asp
                100                 105                 110

His Asn Val Gln Ala Tyr Val Phe Thr Asp Tyr Trp Glu Asp Ile Gly
            115                 120                 125

Thr Ile Arg Ser Phe Phe Asp Ala Asn Met Ser Leu Cys Glu Gln Pro
130                 135                 140

Pro Lys Phe Glu Phe Tyr Asp Pro Lys Thr Pro Phe Phe Thr Ser Pro
145                 150                 155                 160

Arg Tyr Leu Pro Pro Thr Lys Ser Asp Lys Cys Arg Ile Lys Glu Ala
                165                 170                 175

Ile Ile Leu His Gly Cys Phe Leu Arg Glu Cys Lys Ile Glu His Ser
                180                 185                 190

Ile Ile Gly Val Pro Ser Arg Leu Asn Ser Gly Ser Glu Leu Lys Asn
            195                 200                 205

Ala Met Met Met Gly Ala Asp Ser Tyr Glu Thr Glu Asp Glu Ile Ser
210                 215                 220

Arg Leu Met Ser Glu Gly Lys Val Pro Ile Gly Val Gly Glu Asn Thr
225                 230                 235                 240

Lys Ile Ser Asn Cys Ile Ile Asp Met Asn Ala Arg Ile Gly Arg Asp
                245                 250                 255

Val Val Ile Ser Asn Lys Glu Gly Val Gln Glu Ala Asp Arg Pro Glu
                260                 265                 270

Glu Gly Tyr Tyr Ile Arg Ser Gly Ile Val Val Ile Gln Lys Asn Ala
            275                 280                 285

Thr Ile Lys Asp Gly Thr Val Val
290                 295
```

(2) INFORMATION FOR SEQ ID NO: 6:

(i) SEQUENCE CHARACTERISTICS:
    (A) LENGTH: 1797 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: FIGURE 4 WE.AGA.7

(xi) SEQUENCE DESCRIPTION: SEQ ID NO: 6:

```
CGTGCGTCTC CCCCGTCAGA GTCGAGGGCT CCGCTGCGAG CGCCTCAAAG GTCGGCGACA      60

CGGCAGCATC AGGCACGACA GGGTCCCAGG AGGATGTGCA ACGGCGGCAG GGGCCCGCCA     120

TACTGGACAG CTGGTGTCAC CTCCGCCCCA GCCCGGCAGA CACCCTTGTT CTCCGGACGT     180

CCTTCAGGAG GATTAAGCGA TCCGAACGAG GTTGCGGCCG TCATACTCGG CGGCGGCACC     240

GGGACTCAGC TCTTCCCACT CACGAGCACA AGGGCCACAC CTGCTGTTCC TATTGGAGGA     300

TGTTACAGGC TCATCGACAT TCCCATGAGC AACTGCTTCA ACAGTGGCAT CAACAAGATA     360

TTCGTCATGA CCCAGTTCAA CTCGGCCTCC CTTAATCGTC ACATTCACCG CACCTACCTC     420

GGCGGGGGAA TCAATTTCAC TGATGGATCC GTTGAGGTAT TGGCCGCGAC GCAAATGCCC     480

GGGGAGGCTG CTGGATGGTT CCGCGGAACA GCGGACGCGT GGAGAAAAAT TATCTGGGTG     540

CTTGAGGACT ATTATAAGAA TAAATCCATA GAGCACATTT TGATCTTGTC GGGCGATCAG     600

CTTTATCGCA TGGATTACAT GGAGCTTGTG CAGAAACATG TGGATGACAA TGCTGACATT     660

ACTTTATCAT GTGCCCCTGT TGGAGAGAGC CGGGCATCTG AGTACGGGCT AGTGAAGTTC     720

GACAGTTCAG GCCGTGTGGT CCAGTTTTCT GAGCAGCCAA AGGGTGACGA TCTGGAAGCG     780

ATGAAAGTGG ACACCAGTTT TCTCAATTTC GCCATCGACG ATCCTGCTAA ATATCCATAC     840

ATTGCTTCTA TGGGAGTCTA TGTCTTCAAA AGAGATGTTC TGCTCAACCT TCTAAAGTCA     900

AGATATGCAG AACTACATGA CTTTGGGTCT GAGATCCTCC CGAGAGCTCT GCATGACCAC     960

AATGTACAGG CTTATGTCTT CACTGACTAC TGGGAGGACA TTGGAACAAT CAGATCCTTC    1020

TTCGATGCAA ACAGGGCCCT CTGCGAGCAG CCCCCAAAGT TCGAGTTTTA TGATCCCAAA    1080

ACTCCCTTCT TCACCTCGCC TCGATACTTG CCACCAACAA AGTCAGACAA GTGCAGGATC    1140

AAAGAAGCGA TCATTCTGCA CGGCTGCTTC TTGCGTGAAT GCAAAATCGA GCACACTGCG    1200

TTCTCACGCC TAAACTCCGG AAGCGAGCTC AAGAATGCGA TGATGATGGG CGCGGACTCG    1260

TACGAGACCG AAGACGAGAT GTCGAGGCTG ATGTCGGAGG GCAAGGTCCC CATCGGCGTC    1320

GGGGAGAACA CAAAGATCAG CAACTGCATC ATCGACATGA ACGCGAGGAT AGGAAGGGAC    1380

GTGGTCATCT CAAACAAGGA GGGAGTGCAA GAAGCCGACA GGCCGGAGGA GGGGTACTAC    1440

ATCAGGTCCG GGATCGTGGT GATCCAGAAG AACGCGACCA TCAAGGACGG CACCGTCGTG    1500

TAGTACCCGG GCCGGCGCGA CGGGGTTCCG CGACAACCTC TCTGCGCTGA TCGTCGTCGT    1560

CGGCTTCTCG GGGCCGGGAC TGGAGGAGTG ACCGGGGACG GGGGGCGTTT GAAGCTTTGA    1620

ATGGCTGAGA CTGAAAGTGG AGGCGCGCGC AGGCAGCATC AGTAGTAAGT AGTAAGTGGT    1680

AGTAAGTAGC AGTGGAACAA AGTAATAGTC GTTCGTTTTG CCCCTGTAAT AAATAAGAAG    1740

AGGCTGTGTG TTGAGGTAAA GAAGTGGCCG CGAGCAAACA AAAAAAAAAA AAAAAAA      1797
```

(2) INFORMATION FOR SEQ ID NO: 7:

(i) SEQUENCE CHARACTERISTICS:
        (A) LENGTH: 500 amino acids

```
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: FIGURE 4 WE.AGA.7

(xi) SEQUENCE DESCRIPTION: SEQ ID NO: 7:

Arg Ala Ser Pro Pro Ser Glu Ser Arg Ala Pro Leu Arg Ala Pro Gln
 1               5                  10                  15

Arg Ser Ala Thr Arg Gln His Gln Ala Arg Gln Gly Pro Arg Arg Met
            20                  25                  30

Cys Asn Gly Gly Arg Gly Pro Pro Tyr Trp Thr Ala Gly Val Thr Ser
            35                  40                  45

Ala Pro Ala Arg Gln Thr Pro Leu Phe Ser Gly Arg Pro Ser Gly Gly
 50                  55                  60

Leu Ser Asp Pro Asn Glu Val Ala Val Ile Leu Gly Gly Gly Thr
 65                  70                  75              80

Gly Thr Gln Leu Phe Pro Leu Thr Ser Thr Arg Ala Thr Pro Ala Val
                85                  90                  95

Pro Ile Gly Gly Cys Tyr Arg Leu Ile Asp Ile Pro Met Ser Asn Cys
                100                 105                 110

Phe Asn Ser Gly Ile Asn Lys Xaa Phe Val Met Thr Gln Phe Asn Ser
            115                 120                 125

Ala Ser Leu Asn Arg His Ile His Arg Thr Tyr Leu Gly Gly Gly Ile
 130                 135                 140

Asn Phe Thr Asp Gly Ser Val Glu Val Leu Ala Ala Thr Gln Met Pro
145                 150                 155                 160

Gly Glu Ala Ala Gly Trp Phe Arg Gly Thr Ala Asp Ala Trp Arg Lys
                165                 170                 175

Ile Ile Trp Val Leu Glu Asp Tyr Tyr Lys Asn Lys Ser Ile Glu His
                180                 185                 190

Ile Leu Ile Leu Ser Gly Asp Gln Leu Tyr Arg Met Asp Tyr Met Glu
                195                 200                 205

Leu Val Gln Lys His Val Asp Asp Asn Ala Asp Ile Thr Leu Ser Cys
 210                 215                 220

Ala Pro Val Gly Glu Ser Arg Ala Ser Glu Tyr Gly Leu Val Lys Phe
225                 230                 235                 240

Asp Ser Ser Gly Arg Val Val Gln Phe Ser Glu Gln Pro Lys Gly Asp
                245                 250                 255

Asp Leu Glu Ala Met Lys Val Asp Thr Ser Phe Leu Asn Phe Ala Ile
                260                 265                 270

Asp Asp Pro Ala Lys Tyr Pro Tyr Ile Ala Ser Met Gly Val Tyr Val
                275                 280                 285

Phe Lys Arg Asp Val Leu Leu Asn Leu Leu Lys Ser Arg Tyr Ala Glu
                290                 295                 300

Leu His Asp Phe Gly Ser Glu Ile Leu Pro Arg Ala Leu His Asp His
305                 310                 315                 320

Asn Val Gln Ala Tyr Val Phe Thr Asp Tyr Trp Glu Asp Ile Gly Thr
                325                 330                 335

Ile Arg Ser Phe Phe Asp Ala Asn Arg Ala Leu Cys Glu Gln Pro Pro
                340                 345                 350

Lys Phe Glu Phe Tyr Asp Pro Lys Thr Pro Phe Thr Ser Pro Arg
                355                 360                 365
```

```
Tyr Leu Pro Pro Thr Lys Ser Asp Lys Cys Arg Ile Lys Glu Ala Ile
            370                 375                 380

Ile Leu His Gly Cys Phe Leu Arg Glu Cys Lys Ile Glu His Thr Ala
385                 390                 395                 400

Phe Ser Arg Leu Asn Ser Gly Ser Glu Leu Lys Asn Ala Met Met Met
                405                 410                 415

Gly Ala Asp Ser Tyr Glu Thr Glu Asp Glu Met Ser Arg Leu Met Ser
            420                 425                 430

Glu Gly Lys Val Pro Ile Gly Val Gly Glu Asn Thr Lys Ile Ser Asn
            435                 440                 445

Cys Ile Ile Asp Met Asn Ala Arg Ile Gly Arg Asp Val Val Ile Ser
            450                 455                 460

Asn Lys Glu Gly Val Gln Glu Ala Asp Arg Pro Glu Glu Gly Tyr Tyr
465                 470                 475                 480

Ile Arg Ser Gly Ile Val Val Ile Gln Lys Asn Ala Thr Ile Lys Asp
                485                 490                 495

Gly Thr Val Val
            500
```

(2) INFORMATION FOR SEQ ID NO: 8:

(i) SEQUENCE CHARACTERISTICS:
        (A) LENGTH: 3827 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: FIGURE 5 GSTII PROMOTER (xi) SEQUENCE DESCRIPTION: SEQ ID NO: 8:

```
GAATTCCAAA TATATGATGA TTGTTGTCCT AGTGCAGAAG AACTAAATAT ACTAGCGAAA    60

AAAAACCTTC CTAGTCATGT AAGTGTATGG GCATATAGAA AAATAAACAT CTCAAGACTC   120

CAAACTAGTC ATAGCTTTTA GTCACAACTT CAAACACTTC ATGCCAACAA GATCATGGAT   180

TTTTTTTTTT GCCTAAGACA AAACTAGAAT GAGAAAAGAA CTAACTCATC ATACATATTA   240

GTATGGCATC ACAAAAAAAA TGACACATAT ATGATACTAT ATCACACAGG CCTTCAGTTT   300

CTAGAACAAG TGCAGATCGA TGTGTGGGTA TGCATGTCTA ATATTTTACT AGGTTGGATA   360

TGCATGGGCG TTCATTCAGA ATCAGTTTCA CACAGTTTAT CGCACTTCTG TTTACAAAAC   420

ATGGATTTCA TTGCTCTGTA CTGGCTACAT GCGTAAGGAT CAACTTGTCT AATCTAGGTG   480

CATCCTCCTT GTCAAGCAAA CTTAACAATT TGATAAAAAA AAATGCAGCT TTTATATGTG   540

AACCCATAAC TTAATATGGA CAGGAAACTG ATGTGCAACA ACAAAAACTA AAATAGGAAG   600

GAAACACAAG TTCCAAATGT ATAATAATTG TCACCATAGT GCAAAGAAC CAAATATACT    660

GCAGAGAAAA CTTCCTAGTC ATGTAAGTGT ATGGACATAT AGAAATAAAA CATCTCAAGA   720

CTCCAATAAC AGGCTCAAGC TAACTAGTCA TGGCTTTAAA CCTTCATGAT GCAAACTAGT   780

CACAACTTTA AACATTTCAT GCCAACAAGA TCATGGATGG TGTTTTTTTT TCCTAGGGAA   840

AAGCTAGAAT GAGAAAAGAC CTAACTCAGC ATACATATCA GGATAGTATC GTATAGACAC   900

GTATATGATA CTATATCACG CAGCCGTTCA ATTTCTAGAA CAAATGCAGA TTGATCTGTG   960

AATATGCATG TCTCATATTT TACTAGGTTG GATGGACTGA ATCCCGTGAA ACAAACAATT  1020

TATTCAACAA GTTTCTGCAT GAATATCATC TCAAATTCAA TAATCACTCT CGTTGATAAA  1080
```

-continued

```
AAAAATGCAA CCAACAGTTA ACCAGAAGTG AAATAGAAAC TATTTGAATC AGATCACTCC    1140
GTTATTCACA TCAAAATAAT TGTTGCTTGA TCTATAAAAG CAGTAGGAAC ATTGTTTACC    1200
CATCAATTTC AAGTACACAG TAACAAGAAC AGTACAGCTA GAATTGAGCA TGTGAGTATT    1260
GTTGATACCT CGTTGAGCTC TCTCTGCCGC GGCTTTCTGC TCGGCAGCAA GAGCCAGCTC    1320
AGGATCCACC CCGAAAGCTT GGGCGTAGGT GTTGTCTATC GGCGAAAACA CGCGCGGTAC    1380
GCCAAGAACA GCGCGGCCAT CTCCATCCCA GGCACGGTGC GCCCGCTTTT TCGCCGTCTC    1440
GCTGAGTCAC GGCGGGCGTC CAGCAGGTAG TTGAGCGCCT TCCGCGGCAC GAATCGCTGC    1500
GTGCGGCCCG GATCTGGTCG AGTTGGTAGT CAGCGTCGGT GTCGAATGCC GGGACGTCGA    1560
CCAGGAAGAA GTTGCCGTCG CTGGGGTGGG ACGGAAGGC GTCAGGATTG TCGCAAGGGC     1620
AGAGCCCAGC CTGCGGGCGG GGCTACCTCG TCGACGCCTC GGCACGGCGG CGGCAAAGCT    1680
GCTGCGGGAC GTGCCCGCCT GGGCCGCCTT CTCGGTGAAG TGGTCCTCGA AGGGACGAG     1740
CTCGCTGGGG TCAAACCACC CCATAGCTCG AGTCACCGAA GAAGGCGACG AGGACGAGCC    1800
CGTCGCGGTG GCCGCGGTGT ACCTCCTCGT CGTCGGTGAG GCTGACGCTG TAGATATGGC    1860
CAGGCCACCA CGGATGGGAC TTCACCTTGG CCCAGACCAT GTCGCCGAAC CGGGGCCGC     1920
CGTTCGCCCA TGCGATGCCG CGTCCGGCAG CAGGAACCAT GGCGCCTCCA GCGGCGGGGT    1980
CGGACATCCT GTGGAGGGGA ACCGAAAACC TAGATTTGGA TGCAGGTTCG ATTGGTCTGG    2040
GCTTGGGTTT GGGTTCCGGA GGAGGGTGGC CTGGGATCGG TGGAAGGAGG GACATTGTTG    2100
GTAATTTTTA TTATTTTATA ATATGGAGAA ATTCGAGAGA CTGAACGATG GTGATGTTTA    2160
TTTGAGGACT ATGTAGTATA AAGTGTAAAA TAGTATTTTA TCAAGTTTAT ATTCACGTTT    2220
TTGCTGAAGA TAGTATAATA GTGGAGTTGT TTTTGGCGGC TACATAATCT TAGGCTATCT    2280
TCTCGGTCGC TCTCATATCA TATCTACTAT CACATTCTCT ATTTTAAATT TCACTTTGTG    2340
TAATCTACAC TATAAAATAG TGTTTTACAC GGTATGTTGT ACACAGCCTT ATCGTGGCGC    2400
GACGGAGTTG GATAGAGATG GTGAACAGCT GGATAGATAT GATTTATAGG CGATTGGGTA    2460
GATGTGATTT GATAGGTGGT TATGTAGGAG CGATTTAGTG AGACATTGTA ATAATTAGG     2520
TTGATGTGAT CCGAGGATGG CTAGGTAGAT ATGATTTTAA TGGATGGTTT GGTGGACTAA    2580
GTTATGTGGA CATTATAATA TGTTTTAAAT TTCTAAGAAA TTGTTTGTGT TAATTGTAT     2640
CCCACATAGA TTATTTAGCC ATCTCAAAGA GAGGTTTGGG TTGTTTACAC AAATAAAATA    2700
TTCGTTTGCT TCTACAATTT ATATGTTTTT TATTTACATG AAAACTATAT TTTTTATTCA    2760
TCTACTCACC CAGCACAGAA ATTCTGGTTG AGTAGATGAA AAAAAACTAC AACAAACTCT    2820
TCCTGAAAGT GTCGGTGTGA AGCCGAGAAA TCCTTTTCAT TTCGGTGACG GAGCCCCTTG    2880
CTGGCTGCTG CTCAGTGCAC TCCGTTCGCC TGCCTGCCAC TACAAGCGAC GGCCGACGAC    2940
TCGCAAGTAT CGGTAGGCAT TTTAAAACTG AAAACCAAAT CTAAACCCGA ATAGACCAAA    3000
TTGTTGGTTT ATTCGGGTTT TTGGGTTCGG ATTCGGTTTC TAAATATGCT ATATTTTAGG    3060
GTATAGGTTC GGGTTCAGTT TCTAACCTTT AAAACCTGAA TAGACGAATA ACCCGAAATA    3120
TAAAAAATCT CTTAATATGT GATGATATTA TTATATGATT TATGAACTTA TTAACCGAAA    3180
ATAATGATAC CATCCTAACG ATAGTATATA TATCTATGTA TGCTATTTTT ATAGTCACTT    3240
GTTGTAATAA TAGTACTTCC AATTAATTAA TCAGTGTATA TATTTTAACA AAAGATACTA    3300
GCCTCTCTAC TATTTGAGTA TATTCGGTGC ACCGAATAGA CCGAACCGAA ATTGTAAGTC    3360
TATTCAGGTT CGGTTCCTAA AATTATTTTA AAAATTTTGG TTCTCATATT TCAGAATCCG    3420
```

| | | | | |
|---|---|---|---|---|
| AAATTTCATA | AATCCAAATA | GACCGAACCA | AATTACGCTA | ATAGACCGAA TAACTAGCGT | 3480 |
| ACTCGCAAGT | CGCACCCCAC | TAGCCTGCTG | CGTGCGTAAG | CGAGGACGTC ACGCGTTCTC | 3540 |
| CCTCCCGTCG | ACCAAATACA | CTTGGTCTTC | TAGCACCTTC | TTCCTCTCCA AGACTCCAAT | 3600 |
| CCCCCAACCA | CCAGAACCAG | CGCCAGCTCT | AACGTCACCT | CTGATTTCTC TCTCCTCTCT | 3660 |
| ATTGCTAGCT | GCTTTATTAT | AAGTAGCAGC | TGCAGCAGGC | AGGAGCTGCA CACACCCATC | 3720 |
| CAATTCCAGC | TGCTGATCTT | GATCCTGCAC | CCCGAGCCGT | ACACAAGAGC TAGTCGGTAG | 3780 |
| AACTTGCAGG | AGCGGAGCAG | AACTAAGTGC | AGAGAACAGG | ACATATG | 3827 |

(2) INFORMATION FOR SEQ ID NO: 9:

(i) SEQUENCE CHARACTERISTICS:
        (A) LENGTH: 954 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 9:

| | | | | |
|---|---|---|---|---|
| CCAGCTGCTG | ATCTTGATCC | TGCACCCCGA | GCCGTACACA | AGAGCTAGTC GGTAGAACTT | 60 |
| GCAGGAGCGG | AGCAGAACTA | AGTGCAGAGA | ACAGGACATA | TGGCTACGCC GGCGGTGAAG | 120 |
| GTTTACGGGT | GGGCTATCTC | GCCGTTCGTA | TCGCGGGCTC | TGCTGGCCCT GGAGGAGGCC | 180 |
| GGCGTCGACT | ACGAGCTCGT | CCCCATGAGC | CGCCAGGACG | GCGACCACCG CCGCCCGGAG | 240 |
| CACCTCGCCA | GGAACCCTTT | CGGGAAGGTG | CCGGTGCTCG | AGGATGGCGA CCTCACGCTC | 300 |
| TTCGAATCAC | GTGCGATCGC | GAGGCATGTT | CTCCGGAAGC | ACAAGCCGGA GCTGCTGGGC | 360 |
| GGCGGCAGGC | TGGAGCAGAC | GGCGATGGTG | GACGTGTGGC | TGGAGGTGGA GGCCCACCAG | 420 |
| CTGAGCCCGC | CGGCGATCGC | CATCGTGGTG | GAGTGCGTGT | TCGCGCCGTT CCTGGGCCGC | 480 |
| GAGCGCAACC | AGGCGGTGGT | GGACGAGAAC | GTGGAGAAGC | TCAAGAAGGT GCTGGAGGTG | 540 |
| TACGAGGCGC | GGCTGGCCAC | GTGCACGTAC | CTCGCCGGCG | ACTTCCTCAG CCTCGCCGAC | 600 |
| CTCAGCCCCT | TCACCATCAT | GCACTGCCTC | ATGGCCACCG | AGTACGCCGC TCTCGTCCAT | 660 |
| GCGCTCCCGC | ACGTCAGCGC | CTGGTGGCAG | GGCCTCGCCG | CGCGCCCGGC GGCCAACAAG | 720 |
| GTGGCGCAGT | TCATGCCGGT | CGGCGCCGGA | GCGCCCAAGG | AACAGGAGTG ACGATGAAGC | 780 |
| GATCGAAGCG | ACTTGTGTTG | TTGTGCTTGA | TTAGTTAATT | GGAAACCTTC TCACTCATCT | 840 |
| AGTCCATCAT | GGTGCCTGCT | TTTCTTTATA | CTATTTGTCT | TAATTTTGCT GCTTTCTCCA | 900 |
| CGGAATAATA | GTAGAGATTT | GGAAATGTAA | TGTATTTATC | AAAAAAAAAA AAAA | 954 |

(2) INFORMATION FOR SEQ ID NO: 10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: PAGE 7 LINE 14 GLGA (xi) SEQUENCE DESCRIPTION: SEQ ID NO: 10:

GATAATGCAG          10

(2) INFORMATION FOR SEQ ID NO: 11:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (ii) MOLECULE TYPE: cDNA (vi) ORIGINAL SOURCE:
    (A) ORGANISM: PAGE 7 LINE 15 CONSENSUS (xi) SEQUENCE DESCRIPTION: SEQ ID NO: 11:

AACAATGGCT                                                          10

(2) INFORMATION FOR SEQ ID NO: 12:

(i) SEQUENCE CHARACTERISTICS:
        (A) LENGTH: 56 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: PAGE 7 LINE 23 CONSENSUS RUBISCO SSU (xi) SEQUENCE DESCRIPTION: SEQ ID NO: 12:

Met Ala Ser Ser Met Leu Ser Ser Ala Ala Val Ala Thr Arg Thr Asn
1               5                   10                  15

Pro Ala Gln Ala Ser Met Val Ala Pro Phe Thr Gly Leu Lys Ser Ala
            20                  25                  30

Ala Phe Pro Val Ser Arg Lys Gln Asn Leu Asp Ile Thr Ser Ile Ala
        35                  40                  45

Ser Asn Gly Gly Arg Val Gln Cys
    50                  55

(2) INFORMATION FOR SEQ ID NO: 13:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: PAGE 7 LINE 27 CORN RUBISCO SSU (xi) SEQUENCE DESCRIPTION: SEQ ID NO: 13:

Met Ala Pro Thr Val Met Met Ala Ser Ser Ala Thr Ala Thr Arg Thr
1               5                   10                  15

Asn Pro Ala Gln Ala Ser Ala Val Ala Pro Phe Gln Gly Leu Lys Ser
            20                  25                  30

Thr Ala Ser Leu Pro Val Ala Arg Arg Ser Ser Arg Ser Leu Gly Asn
        35                  40                  45

Val Ala Asn Gly Gly Arg Ile Arg Cys
    50                  55

(2) INFORMATION FOR SEQ ID NO: 14:

(i) SEQUENCE CHARACTERISTICS:
        (A) LENGTH: 73 amino acids
        (B) TYPE: amino acid
        (C) STRANDEDNESS: single

```
        (D) TOPOLOGY: linear (ii) MOLECULE TYPE: peptide (vi) ORIGINAL SOURCE:
         (A) ORGANISM: PAGE 7 LINE 29 STARCH SYNTHASE (xi) SEQUENCE DESCRIPTION: SEQ ID NO: 14:

Met Ala Ala Leu Ala Thr Ser Gln Leu Val Ala Thr Arg Ala Gly Leu
1               5                   10                  15

Gly Val Pro Asp Ala Ser Thr Phe Arg Arg Gly Ala Ala Gln Gly Leu
            20                  25                  30

Arg Gly Ala Arg Ala Ser Ala Ala Ala Asp Thr Leu Ser Met Arg Thr
        35                  40                  45

Ala Ser Ala Arg Ala Ala Pro Arg His Gln Gln Ala Arg Arg Gly
    50                  55                  60

Gly Arg Phe Pro Ser Leu Val Val Cys
65                  70

(2) INFORMATION FOR SEQ ID NO: 15:

(i) SEQUENCE CHARACTERISTICS:
        (A) LENGTH: 58 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: PAGE 7 LINE 32 G-3-P (xi) SEQUENCE DESCRIPTION: SEQ ID NO: 15:

Met Ala Gln Ile Leu Ala Pro Ser Thr Gln Trp Gln Met Arg Ile Thr
1               5                   10                  15

Lys Thr Ser Pro Cys Ala Thr Pro Ile Thr Ser Lys Met Trp Ser Ser
            20                  25                  30

Leu Val Met Lys Gln Thr Lys Lys Val Ala His Ser Ala Lys Phe Arg
        35                  40                  45

Val Met Ala Val Asn Ser Glu Asn Gly Thr
    50                  55

(2) INFORMATION FOR SEQ ID NO: 16:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: PAGE 7 LINE 38 ADPG PP (xi) SEQUENCE DESCRIPTION: SEQ ID NO: 16:

Arg Ala Ser Pro Pro Ser Glu Ser Arg Ala Pro Leu Arg Ala Pro Gln
1               5                   10                  15

Arg Ser Ala Thr Arg Gln His Gln Ala Arg Gln Gly Pro Arg Met
            20                  25                  30

Cys (2) INFORMATION FOR SEQ ID NO: 17:
```

(i) SEQUENCE CHARACTERISTICS:
            (A) LENGTH: 22 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: PAGE 8 LINE 28-29 MAIZE B73

(xi) SEQUENCE DESCRIPTION: SEQ ID NO: 17:

Ala Ala Ala Arg Lys Ala Val Met Val Pro Glu Gly Glu Asn Arg Glu
1               5                   10                  15

Phe Val Lys Tyr Leu Phe
            20

(2) INFORMATION FOR SEQ ID NO: 18:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: PAGE 8 LINE 31 BE FRAGMENT 1

(xi) SEQUENCE DESCRIPTION: SEQ ID NO: 18:

Val Arg Pro Pro Pro Xaa Asp Gly Asp Gly Ile Phe Ile
1               5                   10

(2) INFORMATION FOR SEQ ID NO: 19:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: PAGE  8 LINE 32 B FRAGMENT 2

(xi) SEQUENCE DESCRIPTION: SEQ ID NO: 19:

Gln Gly His Leu Xaa Gln Tyr Tyr
1               5

(2) INFORMATION FOR SEQ ID NO: 20:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: PAGE 8 LINE 33 B FRAGMENT 3

(xi) SEQUENCE DESCRIPTION: SEQ ID NO: 20:

Ile Phe Gln Ile Asp Pro Met Leu Ser Thr Tyr Lys Tyr
1               5                   10

(2) INFORMATION FOR SEQ ID NO: 21:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (vi) ORIGINAL SOURCE:
    (A) ORGANISM: PAGE 9 LINE 10 ADPG BINDING SITE (xi) SEQUENCE DESCRIPTION: SEQ ID NO: 21:

Lys Thr Gly Gly Leu
1               5

(2) INFORMATION FOR SEQ ID NO: 22:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: PAGE 9 LINE 11 PEA STARCH SYNTHASE (xi) SEQUENCE DESCRIPTION: SEQ ID NO: 22:

Gly Glu Lys Pro Pro Pro Leu Ala Gly Thr Asn Val Met Asn Ile Ile
1               5                   10                  15

Leu Val Ser Ala Glu Cys Ala Pro Trp Ser Lys Thr Gly Gly Leu Gly
            20                  25                  30

Asp Val Ala Gly Ser Leu Pro Lys Ala Leu
        35                  40

(2) INFORMATION FOR SEQ ID NO: 23:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: PAGE 9 LINE 12 MAIZE STARCH SYNTHASE (xi) SEQUENCE DESCRIPTION: SEQ ID NO: 23:

Ala Ser Ala Gly Met Asn Val Val Phe Val Gly Ala Glu Met Ala Pro
1               5                   10                  15

Trp Ser Lys Thr Gly Gly Leu Gly Asp Val Leu Gly Gly Leu Pro
            20                  25                  30

(2) INFORMATION FOR SEQ ID NO: 24:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: PAGE 9 LINE 13 BARLEY STARCH SYNTHASE (xi) SEQUENCE DESCRIPTION: SEQ ID NO: 24:

```
Ala Thr Gly Ser Gly Met Asn Leu Val Phe Val Gly Ala Glu Met Ala
1               5                   10                  15

Pro Trp Ser Lys Thr Gly Gly Leu Gly Asp Val Leu Gly Gly Leu Pro
                20                  25                  30

(2) INFORMATION FOR SEQ ID NO: 25:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: PAGE 9 LINE 14 POTATO STARCH SYNTHASE (xi) SEQUENCE DESCRIPTION: SEQ ID NO: 25:

Gly Lys Gly Met Asn Leu Ile Phe Val Gly Thr Glu Val Gly Pro Glu
1               5                   10                  15

Ser Lys Thr Gly Gly Leu Gly Asp Val Leu Gly Gly Leu Pro
                20                  25                  30

(2) INFORMATION FOR SEQ ID NO: 26:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: PAGE 9 LINE 15 E COLI STARCH SYNTHASE (xi) SEQUENCE DESCRIPTION: SEQ ID NO: 26:

Met Gln Val Leu His Val Cys Ser Glu Met Phe Pro Leu Leu Lys Thr
1               5                   10                  15

Gly Gly Leu Ala Asp Val Ile Gly Ala Leu Pro
                20                  25

(2) INFORMATION FOR SEQ ID NO: 27:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: PAGE 9 line34

(xi) SEQUENCE DESCRIPTION: SEQ ID NO: 27:

Ala Glu Leu Ser Arg Glu Gly Pro Ala Pro Arg
1               5                   10

(2) INFORMATION FOR SEQ ID NO: 28:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide
```

(vi) ORIGINAL SOURCE:
            (A) ORGANISM: PAGE 9 line34 internal-1

(xi) SEQUENCE DESCRIPTION: SEQ ID NO: 28:

Lys Asn Tyr Ala Asn Ala Phe Tyr Thr Glu Thr His Ile
1               5                   10

(2) INFORMATION FOR SEQ ID NO: 29:

(i) SEQUENCE CHARACTERISTICS:
            (A) LENGTH: 33 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: PAGE 9 line34 internal-2

(xi) SEQUENCE DESCRIPTION: SEQ ID NO: 29:

Glu Leu Gly Gly Tyr Ile Tyr Gly Gln Asn Asp Met Phe Val Val Asn
1               5                   10                  15

Asn Asp His Ala Ser Leu Val Pro Val Leu Leu Ala Ala Lys Tyr
            20                  25                  30

Ile Arg (2) INFORMATION FOR SEQ ID NO: 30:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (vi) ORIGINAL SOURCE:
            (A) ORGANISM: PAGE 9 line34 internal-3

(xi) SEQUENCE DESCRIPTION: SEQ ID NO: 30:

Glu Val Tyr Tyr Ala Glu Gly Gly Ser Glu Leu Asn Glu Leu Leu
1               5                   10                  15

(2) INFORMATION FOR SEQ ID NO: 31:

(i) SEQUENCE CHARACTERISTICS:
            (A) LENGTH: 310 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: PAGE 9 lines 40-43

(xi) SEQUENCE DESCRIPTION: SEQ ID NO: 31:

CCGCCCGTGC CCGACGCCGG CCTGGGGGTC CTCGGTCTCG AACCTGAAGG GATTGCTGAA      60

GGTTCCATCG ATAACACAGT AGTTGTGGCA AGTGAGCAAG ATTCTGAGAT TGTGGTTGGA     120

AAGGAGCAAG CTCGAGCTAA AGTAACACAA AACATTGTCT TTGTAACGGC GAAACGTCTC     180

CNNNNGCAAA GTCTGGGGGT CTAGGAGATC TTTGTGGTTC ATTGCCAGAA GCTCTTGCTG     240

CTCGTGGTCA CCGTGTGATG GTTGTAATGC CCAGATATTT AAATAATACC TCCGATAGAT     300

TAGCAAANCG                                                            310

(2) INFORMATION FOR SEQ ID NO: 32:

(i) SEQUENCE CHARACTERISTICS:
        (A) LENGTH: 384 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: PAGE 10 lines 6-13

(xi) SEQUENCE DESCRIPTION: SEQ ID NO: 32:

```
CCACGCGTCC GGGTTTGATG CAGTATGCTC GCTCTGTGCT TGTGATACAC AACATTGCTC      60
ATCAGGGTCG TGGCCCTGTA GACGACTTCG TCAATTTTNA CTTGCCTGAA CACTACATCG     120
ACCACTTCAA ACTGTATGAC AACATTGGTG GGGATCACAG CAACGTTTTT GCTGCGGGGC     180
TGAAGACGGC AGACCGGGTG GTGACCGTTA GCAATGGCTA CATGTGGGAG CTGAAGACTT     240
CGGAAGGCGG GTGGGGCCTC CACGACATCA TAAACCAGAA CGACTGGAAG CTGCAGGGCA     300
TCGTGAACGG CATCGACATG AGCGAGTGGA ACCCCGCTGT NGACGTGCAC CTCCACTCCG     360
ACGNCTACAC CAACTACACG TTCG                                            384
```

(2) INFORMATION FOR SEQ ID NO: 33:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: PAGE 11 T1

(xi) SEQUENCE DESCRIPTION: SEQ ID NO: 33:

```
Tyr Val Asn Ala Val Met Thr Ile Pro Lys
1               5                   10
```

(2) INFORMATION FOR SEQ ID NO: 34:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: PAGE 11 T2

(xi) SEQUENCE DESCRIPTION: SEQ ID NO: 34:

```
Glu Gly Ala Asn Phe Val Xaa Gly Tyr Pro Phe Ser Leu Arg
1               5                   10
```

(2) INFORMATION FOR SEQ ID NO: 35:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide

```
    (vi) ORIGINAL SOURCE:
         (A) ORGANISM: PAGE 11 T3

(xi) SEQUENCE DESCRIPTION: SEQ ID NO: 35:

Tyr Xaa Xaa Met Trp Ala Gly Trp Thr Val Lys
1               5                   10

(2) INFORMATION FOR SEQ ID NO: 36:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: PAGE 11 T4

(xi) SEQUENCE DESCRIPTION: SEQ ID NO: 36:

Glu Gly Ala His Thr Ala Val Ser His Gly Leu Trp Leu Asn Ile Pro
1               5                   10                  15
Asp Tyr Asp Ala Pro Thr Gln Leu Val Lys Pro Lys
            20                  25

(2) INFORMATION FOR SEQ ID NO: 37:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: PAGE 11 T5

(xi) SEQUENCE DESCRIPTION: SEQ ID NO: 37:

Leu Gly Asp Ala Met Val Thr Trp Ile Glu Ala Trp Asp Glu Leu Asn
1               5                   10                  15
Pro Ser Thr Pro Ala Ala Ala Asp Gly Lys
            20                  25

(2) INFORMATION FOR SEQ ID NO: 38:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: PAGE 11 T6

(xi) SEQUENCE DESCRIPTION: SEQ ID NO: 38:

Leu Gly Asp Ala Met Val Thr Asp Ile Glu Ala Ala Asp Glu Leu Asn
1               5                   10                  15
Pro Ala Gly Pro Xaa Xaa Xaa Xaa Lys
            20                  25

(2) INFORMATION FOR SEQ ID NO: 39:

(i) SEQUENCE CHARACTERISTICS:
```

(A) LENGTH: 33 amino acids
(B) TYPE: amino acid
(C) STRANDEDNESS: single
(D) TOPOLOGY: linear (ii) MOLECULE TYPE: peptide (vi) ORIGINAL SOURCE:
    (A) ORGANISM: PAGE 11 T7

(xi) SEQUENCE DESCRIPTION: SEQ ID NO: 39:

```
Asn Leu Leu Ser Pro Ser Thr Pro Phe Phe Asn Thr Leu Tyr Asp
1               5                   10                  15
Pro Tyr Arg Glu Gly Ala Asn Phe Val Xaa Gly Tyr Pro Phe Ser Leu
            20                  25                  30
Arg
```

(2) INFORMATION FOR SEQ ID NO: 40:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: PAGE 11 T8

(xi) SEQUENCE DESCRIPTION: SEQ ID NO: 40:

```
Gly Ile Phe Trp Gln Glu Asp Ile Ile Pro Phe Phe Gln Asn Val Thr
1               5                   10                  15
Ile Pro Lys
```

(2) INFORMATION FOR SEQ ID NO: 41:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: PAGE 11 T9

(xi) SEQUENCE DESCRIPTION: SEQ ID NO: 41:

```
Asn Leu Asp Phe Leu Glu Met Trp Arg Pro Phe Phe Gln Pro Tyr His
1               5                   10                  15
Leu Ile Ile Val Gln Asp Gly Asp Pro Thr Lys
            20                  25
```

(2) INFORMATION FOR SEQ ID NO: 42:

(i) SEQUENCE CHARACTERISTICS:
        (A) LENGTH: 420 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: PAGE 12 TABLE 1

(xi) SEQUENCE DESCRIPTION: SEQ ID NO: 42:

```
                                         -continued

TGAACTTGGC CTTTGACCGT GAGCTCATTG GTCCGGCTAT GTACTTCGGT CTCCTGGGTG        60

ATGGTCAGCC TATTGGTCGC TACGACGATA TGTGGGCTGG GTGGTGTGTC AAGGTGATCT       120

GTGATCATTT GGGATTGGGA GTGAAGACGG GTCTTCCCTA CATCTACCAC AGCAAGGCGA       180

GCAACCCATT TGTGAACCTG AAGAAGGAGT ACAAGGGAAT TTTCTGGCAG GAGGACATCA       240

TGCCTTTCTT CCAGAGTGCA AAGCTCTCGA AGAAGCTGT GACGGTTCAA CAATGCTACA        300

TTGAGCTGTC CAAGATGGTG AAGGAGAAGC TTAGCGCCAT TGATCCTTAC TTTGACAAGC       360

TTGCTGATGC TATGGTGACT TGGATTGACG CTTGGGATGT GCTTAACCCG GCCACATAAG       420

(2) INFORMATION FOR SEQ ID NO: 43:

(i) SEQUENCE CHARACTERISTICS:
        (A) LENGTH: 245 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: PAGE 12 TABLE 2

(xi) SEQUENCE DESCRIPTION: SEQ ID NO: 43:

CTTCCGTTCT TCTTTAACAC CTTGTACGAT CCCTACCGTG AAGGTGCTGA CTTCGTCCGT        60

GGATACCCTT TCAGTCTCCG TGAGGGTGTT TCCACTGCTG TTTCTCACGG TCTCGGGCTC       120

AACATCCCTG ATTACGACGC CCCAACTCAA CTCGTCAAGC CTAAGGAAAG AAACACAAGG       180

TATGTGGATG CTGTCATGAC CATCCCAAAG GAACACCTTT GGCCAATTGT GTGGCATGAA       240

CTGCC                                                                  245
```

FOOD PRODUCTS CONTAINING ALTERED STARCH

This is a continuation of application Ser. No. 08/346,602, filed Nov. 29, 1994, now abandoned, which is a continuation-in-part of U.S. patent application Ser. No. 08/263,921 filed on Jun. 21, 1994, now abandoned.

This invention relates to novel plants having an altered ability to produce starch, including an improved ability to produce structurally-altered starch or starch of altered quality. The invention further relates to processes for obtaining such plants.

Agriculture uses many crop plants for the production of food for human or animal consumption, for commercial processes yielding products for human consumption, for the development of industrial products and for other purposes. Traditionally, the improvement of crop plant species involves the introduction of desired traits by genetic crosses. These breeding techniques are highly successful, and seed producers sell the resulting seed to the farmer. The farmer plants this seed and harvests the crop, be it the whole plant, its seed or its fruit. The crop is then used for the various applications mentioned above.

Starch is an important end-product of carbon fixation during photosynthesis in leaves and is an important storage product in seeds and fruits. In economic terms, the starch produced by the edible portions of three grain crops, wheat, rice and maize, provide approximately two-thirds of the world's food calculated as calories.

Many types of crops produce and store starch, including cereals, fruit, roots and oilseeds. Starch (amylose and amylopectin) is synthesised in the plastid compartment (the chloroplast in photosynthetic cells or the amyloplast in non-photosynthetic cells). This starch is used to produce a wide range of food products (for human and animal consumption) and industrial products (such as glue). Several crop varieties are known which produce different types of starch. The type or quality of starch makes it suitable for certain purposes, including particular methods of processing or particular end-uses. For example, U.S. Pat. Nos. 4,789,557, 4,790,997, 4,774,328, 4,770,710, 4,798,735, 4,767,849, 4,801,470, 4,789,738, 4,792,458 and 5,009,911 describe naturally-occurring maize mutants producing starches of differing fine structure suitable for use in various food products. Although known mutants produce altered starch, some of these lines are not suitable for crop breeding and/or for the farmers' purposes. For example, they often give relatively poor yields.

Improved crops may be produced by genetic manipulation of plants known to possess other favorable characteristics. By manipulating the expression of one or more starch-synthesising enzyme genes, it is possible to alter the amount and/or type of starch produced in a plant. One or more enzyme gene constructs, which may be of plant, fungal, bacterial or animal origin, are incorporated into the plant genome by sexual crossing or by transformation. The enzyme gene may be an additional copy of the wild-type gene or may encode a modified or allelic or alternative enzyme with improved properties. Incorporation of the enzyme gene construct(s) may have varying effects depending on the amount and type of enzyme gene(s) introduced (in a sense or antisense orientation). It may increase the plant's capacity to produce starch, in particular by altering the temperature optimum for enzyme activity, giving increased yield. It may also result in production of starch with an altered fine structure (or quality) as the exact structure depends on the balance of the different enzymes. The following patent applications describe this concept in detail: U.S. Pat. Nos. 899,931 and 948,280, equivalent to International application number GB92/01881; U.S. Pat. Nos. 435,020 and 930,935, European publication number EPA 368506 (published May 16, 1990); UK patent application number 9218185.8. The disclosures of these applications are hereby incorporated by reference.

So numerous crop lines are known which produce starches of differing fine structure (that is, differing quality). These lines may be naturally-occurring mutants or may have been produced by genetic manipulation (using traditional breeding or biotechnological techniques).

The invention further provides a DNA construct which comprises at least one target gene encoding an enzyme involved in a starch or glycogen biosynthetic pathway and under the control of a gene switch. The following patent applications describe this concept in detail: International application numbers WO 90/08829 and WO 90/08827 and UK number 9223454. The disclosures of these applications are hereby incorporated by reference.

A particular problem with known lines producing structurally-altered starch is that the quantity of starch produced in the crop is relatively low because:
(i) germinability of the seed is poor (due to a lower starch content), and
(ii) the normal functioning of the starch enzymes is disrupted (so a lower yield of starch is deposited in the seed).

Crops with novel starch quality have a new ability to synthesise starch with an altered fine structure. Expression of the target gene(s) (inserted in a sense and/or an anti-sense orientation) effects a change in the activities and/or natural ratios of the enzymes or their isoforms which results in the production of differing qualities of starch. For example, the fine branching structure of starch is determined by the overall activities of the various isoforms of the starch synthases and branching enzymes being expressed during starch deposition in the developing endosperm. Altering the activities and/or ratios of starch synthetase and branching enzyme and/or the source of the enzymes (e.g. replacing maize starch synthase with pea starch synthase) alters the fine-branching structure of the starch.

The invention further provides a DNA construct which comprises at least one target gene encoding an enzyme involved in a starch or glycogen biosynthetic pathway and under the control of a gene switch.

The invention also provides plants transformed with said DNA construct, the seeds and progeny of such plants, and hybrids whose pedigree includes such plants.

Preferably, the target gene encodes one or more of the following enzymes. soluble starch synthase (SSS) (E.C. 2.4.1.21); branching enzyme (BE) (E.C. 2.4.1.18); glycogen synthase (GS) of bacterial origin (E.C. 2.4.1.21) or animal origin (E.C. 2.4.1.11); ADP-glucose pyrophosphorylase; glycogenin, amylogenin or self glucosylating protein (SGP).

The target gene is obtainable from any suitable bacterial, fungal (including yeast), plant or animal source. The target gene may be derived from cDNA or genomic DNA (gDNA) encoding a starch or glycogen synthetic enzyme, or it may be synthesised ab initio using standard techniques.

The target gene encodes at least part of an enzyme involved in a starch or glycogen biosynthetic pathway. The target gene may encode the complete enzyme in the sense orientation so that the transcription product (mRNA) can be translated into the active enzyme. Alternatively, the target gene may encode a portion of the enzyme in the sense orientation or may encode some or all of the enzyme in the antisense orientation so that the transcribed mRNA inhibits expression of the enzyme. It is possible to insert more than one copy of the target gene into the recipient plant genome. At least one of the target genes may encode a modified allelic form of the enzyme having altered characteristics (such as increased or decreased activity, or differing interactions with other enzymes).

When the enzyme encoded by the target gene must be expressed within the plastid compartment, the protein must be transported into the amyloplast (or chloroplast) by means of a transit peptide. A suitable transit peptide-encoding sequence must therefore precede the target gene sequence.

The above method is generally applicable to all plants producing or storing starch. The recipient plant may be: a cereal such as maize (corn), wheat, rice, sorghum or barley; a fruit-producing species such as banana, apple, tomato or pear; a root crop such as cassava, potato, yam or turnip; an oilseed crop such as rapeseed, sunflower, oil palm, coconut, linseed or groundnut; a meal crop such as soya, bean or pea; or any other suitable species. Preferably the recipient plant is of the family Gramineae and most preferably of the species *Zea mays*.

The method according to the invention may be used to produce a plant having a new ability to synthesise starch with an altered fine structure. The plant has novel starch quality. It is thus possible to generate crops at will which produce starch better adapted or targetted to the crops' end-use (such as starch for varying food products, with improved processing properties, with improved digestibility, with improved seed production characteristics, etc).

As stated previously, a particular problem with known lines producing structurally-altered starch is that the quantity of starch produced in the crop is relatively low because:

(i) germinability of the seed is poor (due to a lower starch content), and (ii) the normal functioning of the starch enzymes is disrupted (so a lower yield of starch is deposited in the seed).

By virtue of this invention, it is possible to alter starch fine structure during seed development without seriously disrupting starch yield. This is achieved by partially down-regulating activities of specific combinations of starch synthesizing enzymes, enough to alter structure without affecting overall flux of carbon to starch. Hence structure is affected without adversely affecting yield.

The farmer benefits from improved starch quality ("improved" with respect to its intended end-use). The main advantage of the novel quality crops described above is that plant growth and vigor is guaranteed in the seed production fields and in the farmers' fields, while allowing the farmer to produce seed with altered starch fine structure/improved starch quality.

In a particularly preferred embodiment of the invention there is provided a corn plant comprising a genome containing various combinations of mutations in enzymes active in the biosynthesis of starch such that, in its altered state, said plant produces seed of the novel starch phenotype.

BRIEF DESCRIPTION OF THE DRAWINGS

FIG. 1 shows the nucleotide sequence for *E. coli* glycogen synthase (SEQ ID NO: 1).

Figure 2:
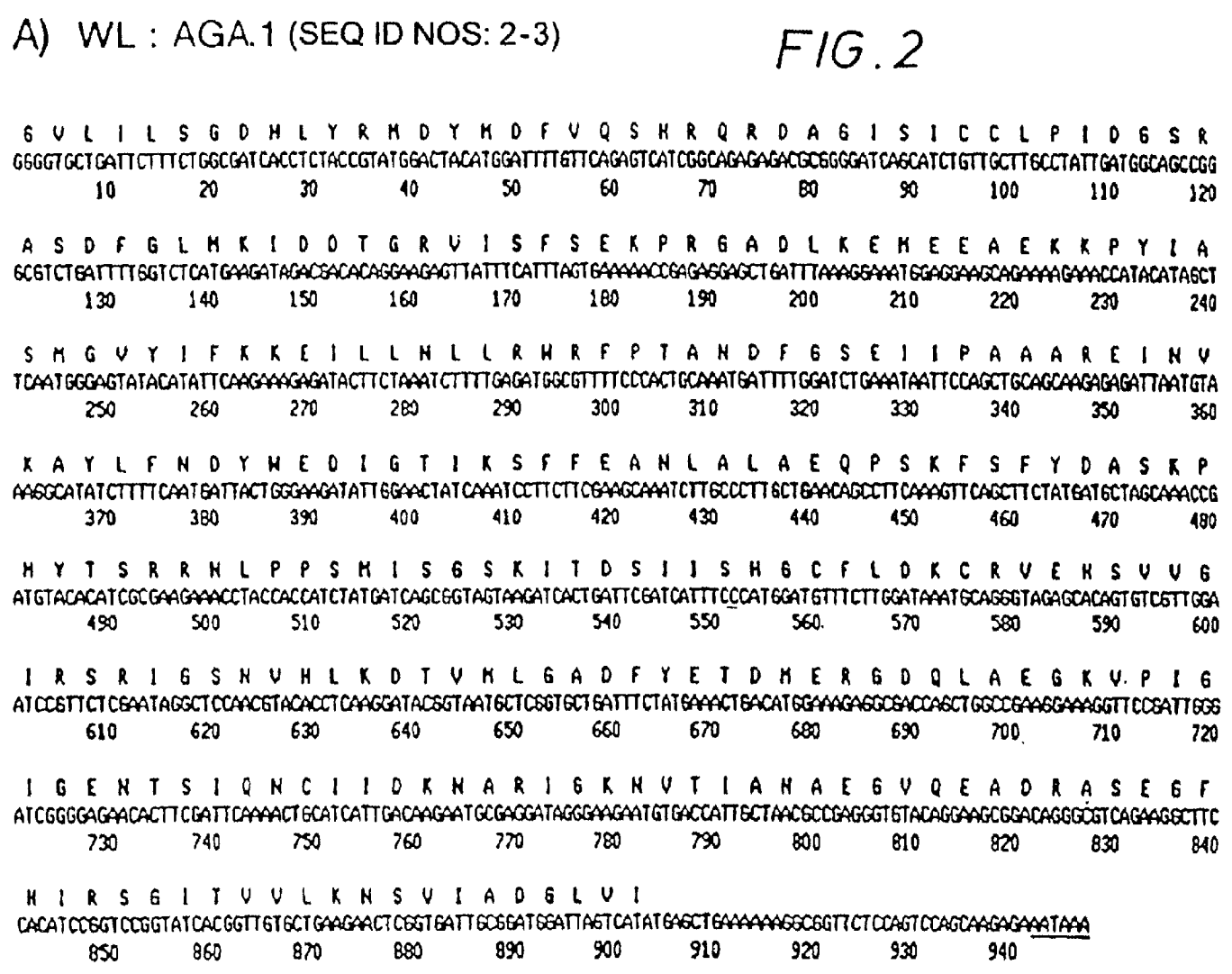

FIG. 2 shows the cDNA sequence of wheat leaf ADP-glucose pyrophosphorylase (clone WL.AGA.1) (SEQ ID NO's 2–3).

FIG. 3 shows the cDNA sequence of wheat leaf ADP-glucose pyrophosphorylase (clone WE.AGA.3) (SEQ ID NO's 4–5).

FIG. 4 shows the cDNA sequence of wheat endosperm ADP-glucose pyrophosphorylase (clone WE.AGA.7) (SEQ ID NO's 6–7).

FIG. 5 shows the sequence for the GST II promotor construct.

FIG. 6 corresponds to the cDNA sequence shown in SEQ ID NO: 9.

FIG. 9 show GUS activity in endosperm.

EFFECTS ON STARCH FINE STRUCTURE

Figure 7:
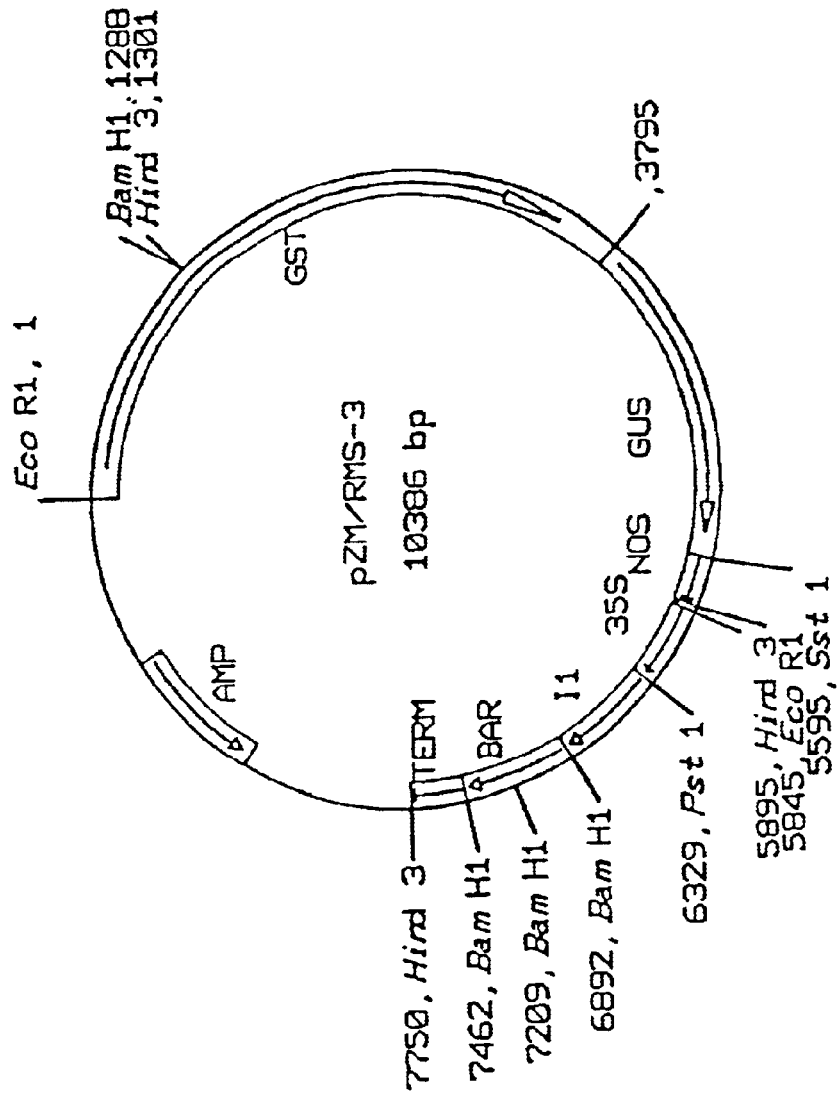
FIG. 7 shows construct pZM/RMS-3 containing the GUS reporter gene.
Figure 8:
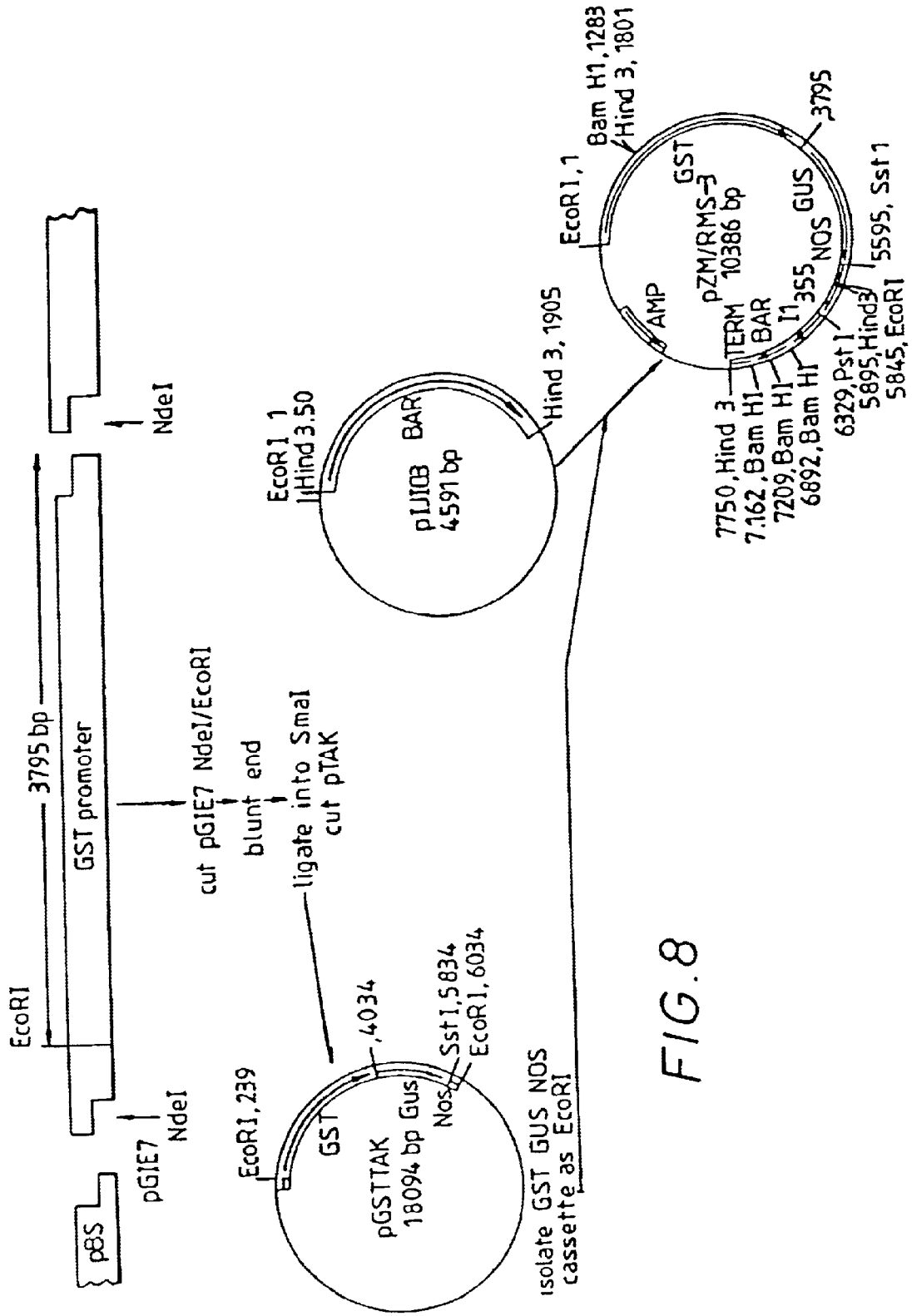
FIG. 8 shows the construction of pZM/RMS-3.

This invention is directed primarily at alteration of starch fine structure. In cereal crops, changing the ratios and activities of SSS and BE and/or the source of the enzymes (e.g. replacing maize SSS with pea SSS) alters the fine-branching structure of the starch. For example, the fine branching structure of starch is determined by the overall activities of the various isoforms of the SSS and BE enzymes being expressed during starch deposition in the developing endosperm. Altering the ratios of these isoforms may be achieved by inter-crossing the starch mutants of corn and making use of the triploid nature of the endosperm tissue. Altering the ratios of these isoforms may also be achieved by standard cloning techniques combined with transformation techniques in which some of the natural enzyme activities are repressed whilst others are over-expressed in a manner analogous to the changes reported herein for the starch mutants of corn. The gene promoters and other regulatory sequences may also be altered to achieve increased amounts of the enzyme in the recipient plant.

Examples of using changes in gene-dosage to effect a change in ratios of activities of isoforms of enyzmes have been acheived using mutations available in maize. This work relies on the well known fact that endosperm tissue is triploid by virtue of receiving two haploid nuclei from the maternal side and one haploid nucleus from the paternal side. The mutations called shrunken-2 (sh2), brittle-2 (bt2), dull (du), sugary (su), waxy (wx) and amylose extender (ae) encode isoforms of ADP glucose pyrophosphorylase, debranching enzyme, soluble starch synthase, bound starch synthase and branching enzyme. The Brittle-2 and Shrunken-2 gene encodes one subunit of ADP glucose pyrophosphorylase, the Sugary locus alters expression levels of debranching enzyme and soluble starch synthase, the Waxy gene encodes granule bound starch synthase, whereas the Amylose Extender gene encodes one isoform of branching enzyme, and the Dull gene alters expression of an isoform of soluble starch synthase as well as a debranching enzyme. When these mutants are crossed with wild-type plants, the inheritance patterns of the mutant gene and wild-type gene depends on whether the gene is paternal or maternal in origin. For example in endosperm cells, where there are three doses of each allele, if the mutant is selfed the cells will all inherit 3 mutant genes (mmm). If instead the wild-type plant is used as a source of pollen for the mutant then there will be 2 doses of mutant allele and 1 dose of wild type allele (mm+). With the mutant as the pollen source, and the wild-type as the female there will be 2 doses of wild-type allelle and 1 dose of mutant allelle (++m). selfing the wild type gives 3 wild-type allelles (+++): Significant new starch types are produced by inter-crossing multiple combinations of mutants. Thus, with each mutation the pollen source may be homozygous recessive for one mutant allelel whilst the female may be homozygous recessive for another mutant allele. For example, with the pollen source as waxy mutant (wxwx) and female amylose extender (aeae), the resulting endosperm tissue will be aeae+:wx++. We herein term this combination-mutant an "Inter-Mutant".

Using known mutants and the gene-dosage crossing regimes we have examined the effects of altered gene expression on starch deposition in grain (See figures). With the bt2 mutant we see a progressive loss in measurable ADPGlc pyrophosphorylase activity which correlates well with a loss in starch synthesis in the grain. The control strength exerted by this enzyme over flux to starch cannot be quantified from these data. In fact our studies indicate that this enzyme is one of the major determinants of the duration of starch synthesis and may have little control over rate of starch synthesis. This mutation does not appreciably alter starch structure. When the mutations are with sugary, dull, waxy and amylose extender we now do detect changes in starch fine strucure (branched chain length changes as well as changes in amylose/amylopectin ratios. In these cases there is more minor control of flux to starch (except with the sugary mutant which is used to make sweet-corn genotypes). In all of these cases it is the changes in ratios of the starch synthases and branching enzymes which have resulted in alterations in starch fine strucure. A dramatic new finding in these studies was the discovery that not only does the mutation reduce expression of key enzymes, but also it induces an overexpression of other enzymes in the pathway. Furthermore, it is only in the full mutant (mmm) genotypes where we see changes in starch fine structure demonstrating that the structural changes occur only when there is an enzyme isoform loss in combination with an enzyme isoform overexpression. Whilst not wishing to be bound by this proposal, these data illustrate the means by which starch structure may be influenced by not only reducing expression (e.g. using antisense constructs) an enzyme but also be simultaneously increasing expression (e.g. using sense construct).

Cloning Enzymes Involved in Starch Biosynthesis

This can be achieved by a variety of known cloning techniques. The source of the special forms of the SSS or BE or GS or amylogenin genes is any organism that can make starch or glycogen. Potential donor organisms are screened and identified. Thereafter there can be two approaches:

(a) via enzyme purification and antibody/sequence generation using the protocol described above.

(b) using SSS and BE and GS and amylogenin cDNAs as heterologous probes to identify the genomic DNAs for SSS and BE and GS and amylogenin in libraries from the organism concerned. The gene transformation, plant regeneration and testing protocols are as described above. In this instance it is necessary to make gene constructs for transformation which contain the regulatory sequences from maize endosperm SSS or BE or another maize endosperm starch synthesis pathway enzyme to ensure expression in endosperm at the correct developmental time (e.g., ADPG pyrophosphorylase).

EXAMPLE 1

Changed Expression of Enzymes of Starch Biosynthesis Pathway in Endosperm Using Inter-Mutants Existing starch mutants include amylose extender (ae), dull (du), sugary (su1 through su4), waxy (wx), brittle-2 (bt2), brittle-1 (bt1), shrunken-2 (sh2),. Inter-mutants are made by crossing one mutant with another in the grain production field. Whilst not wishing to be bound by this proposal, this could be acheived in a variety of ways including, hand-detasseling, genetic male sterility systems, biotech male sterility, chemical male sterility, hand pollinations etc.

EXAMPLE 2

Construction of Plant Transformation Vectors

Plant transformation vectors for use in the method of the invention may be constructed using standard techniques. For example, the GUS reporter gene used in construct pZM/RMS-3 (Example 1) may be replaced with the required starch or glycogen biosynthetic enzyme sequence.

2A Use of Glycogen Synthase

The use of cDNA clones of animal and bacterial glycogen synthases are described in U.S. Pat. No. 948,280 and International patent application publication number GB92/01881. The nucleotide and amino acid sequences of glycogen synthase are known from the literature. For example, FIG. 1 shows the nucleotide sequence for the E coli glgA gene encoding glycogen synthase as retrieved from the GenBank/EMBL (SWISS-PROT) database, accession number J02616 (Kumar et al, 1986, J Biol Chem, 261:16256–16259). E coli glycogen biosynthetic enzyme structural genes were also cloned by Okita et al (1981, J Biol Chem, 256(13):6944–6952). The glycogen synthase glgA structural gene was cloned from *Salmonella typhimurium* LT2 by Leung et al (1987, J Bacteriol, 169(9):4349–4354). The sequences of glycogen synthase from rabbit skeletal muscle (Zhang et al, 1989, FASEB J, 3:2532–2536) and human muscle (Browner et al, 1989, Proc Natl Acad Sci, 86:1443–1447) are also known.

The most favoured sources of the glycogen synthase gene for use in this invention are bacterial rather than animal sources because:

(1) the bacterial glycogen synthase and plant soluble starch synthase both use ADPG, whereas the animal GS enzyme uses UDPG, (2) the bacterial GS and plant SSS enzymes do not have any phosphorylation sites for activation, whereas the animal enzyme does; and, (3) the animal GS enzyme requires glucose-6-phosphate as a co-factor and is allosterically activated, whereas the plant SSS and bacterial GS enzymes are not.

For these reasons the bacterial GS gene is preferred. The bacterial and animal GS sequences are not homologous. The structural genes for the bacterial GS are mapped to pOP12 in E coli and glycogen synthase maps to glgA. Nucleotide sequencing further refined the position of glgA. The translation start point of glgA is known to be immediately following glgC and the nucleotide sequence determined. The $NH_2$ sequence was known so that the actual start of the glgA gene was unambiguously determined as well as confirming the direction of transcription. The deduced amino acid sequence shows complete homology with the known NH2 sequence and with the known amino acid sequence. Different bacterial enzymes show 90% homology. There is complete agreement between the reported and deduced amino acid sequences for the enzyme. Cells transformed with the gene produce a polypeptide that has sequence homology with the known amino acid sequences.

E coli glycogen synthase (FIG. 1) (SEQ ID NO:1) is not a large protein: the structural gene is 1431 base pairs in length, specifying a protein of 477 amino acids with an estimated molecular weight of 49,000. It is known that problems of codon usage can occur with bacterial genes inserted into plant genomes but this is generally not so great with *E coli* genes as with those from other bacteria such as those from Bacillus. Glycogen synthase from *E coli* has a codon usage profile much in common with maize genes but it is preferred to alter, by known procedures, the sequence at the translation start point to be more compatible with a plant consensus sequence:

glgA (SEQ ID NO:10) --- GATAATGCAG cons (SEQ ID NO:11) --- AACAATGGCT

The GS gene construct requires the presence of an amyloplast transit peptide to ensure its correct localisation in the amyloplast. It is believed that chloroplast transit peptides have similar sequences (Heijne et al describe a database of chloroplast transit peptides in 1991, Plant Mol Biol Reporter, 9(2):104–126). Other potential transit peptides are those of ADPG pyrophosphorylase (1991, Plant Mol Biol Reporter, 9:104–126), small subunit RUBISCO, acetolactate synthase, glyceraldehyde-3P-dehy drogenase and nitrite reductase. For example, the consensus sequence of the transit peptide of small subunit RUBISCO from many genotypes has the sequence:

MASSMLSSAAVATRTNPAQASM VAPFTGLKSAAFPVS-RKQNLDI TSIASNGGRVQC and the corn small subunit RUBISCO (SEQ ID NO:13) has the sequence:

MAPTVMMASSATATRTNPAQAS AVAPFQGLKSTASLP-VARRSSR SLGNVASNGGRIRC.

The transit peptide of leaf starch synthase from corn has the sequence: (SEQ ID NO:14)

MAALATSQLVATRAGLGVPDAS TFRRGAAQGLRGA-RASAAADTL SMRTASARAAPRHQQQARRGGR FPSLVVC.

The transit peptide of leaf glyceraldehyde-3P-dehydrogenase from corn (SEQ ID NO:15) has the sequence:

MAQILAPSTQWQMRITKTSPCA TPITSKMWSSLVMKQTKK-VAHS AKFRVMAVNSENGT.

The putative transit peptide from ADPG pyrophosphorylase from wheat (SEQ ID NO:16) has the sequence:

RASPPSESRAPLRAPQRSATRQ HQARQGPRRMC.

2B Use of Branching Enzyme

The use of cDNA clones of plant and bacterial and animal branching enzymes are described in U.S. Pat. No. 948,280 and International patent application publication number GB92/01881. The nucleotide and amino acid sequences for bacterial branching enzymes (BE) are known from the literature. For example, Kiel et al cloned the branching enzyme gene glgB from *Cyanobacterium synechococcus*-sp PCC7942 (1989, Gene (Amst), 78(1):9–18) and from *Bacillus stearothermophilus* (Kiel et al, 1991, Mol Gen Genet, 230(1–2):136–144). The genes glc3 and gha1 of *S cerevisiae* are allelic and encode the glycogen branching enzyme (Rowen et al, 1992, Mol Cell Biol, 12(1):22–29). Matsumomoto et al investigated glycogen branching enzyme from *Neurospora crassa* (1990, J Biochem, 107:118–122). The GenBank/EMBL database also contains sequences for the *E coli* glgB gene encoding branching enzyme.

Branching enzyme [1,4- -D-glucan: 1,4- -D-glucan 6- -D-(1,4- -D-glucano) transferase (E.C. 2.4.1.18)] converts amylose to amylopectin, (a segment of a 1,4- -D-glucan chain is transferred to a primary hydroxyl group in a similar glucan chain) sometimes called Q-enzyme. Like soluble starch synthase, this reaction also has temperature-dependent properties in plants, presumably because of the same molecular mechanisms of helix-to-chain transitions. It is reasonable to believe that the bacterial BE enzyme will behave similarly.

Bacterial branching enzyme genes may be used in this invention, although plant sequences can also be used (rice endosperm: Nakamura et al, 1992, Physiologia Plantarum, 84:329–335 and Nakamura and Yamanouchi, 1992, Plant Physiol, 99:1265–1266; pea: Smith, 1988, Planta, 175:270–279 and Bhattacharyya et al, 1989, J Cell Biochem, Suppl 13D:331; maize endosperm: Singh and Preiss, 1985, Plant Physiology, 79:34–40; Vos-Scherperkeuter et al, 1989, Plant Physiology, 90:75–84; potato: Kossmann et al, 1991, Mol Gen Genet, 230(1–2):39–44; cassava: Salehuzzaman and Visser, 1992, Plant Mol Biol, 20:809–819).

The sequence of maize branching enzyme-I was investigated by Baba et al, 1991, BRC, 181:87–94. Starch branching enzyme-II from maize endosperm was investigated by Fisher et al (1993, Plant Physiol, 102: 1045–1046). We have determined the N-terminal sequences of an 86 kD branching enzyme-II from B73 maize (SEQ ID NO:17) as follows:

Ala-Ala-Ala-Arg-Lys-Al a-Val-Met-Val-Pro-Glu-Gly-Glu-Asn-Arg-Glu-Phe-Val-Lys-Tyr-(Leu)-(Phe) . . .

Fragments from this 86 kD BEII protein from B73 maize are shown below:

1 (SEQ ID NO:18) . . . Val-(Arg)-Pro-Pro-Pro-Xxx-Asp-Gly-Asp-Gly-Ile-Phe-Ile . . .

2 (SEQ ID NO:19) . . . Gln/(Gly)-His-Leu-Xxx-Gln-Tyr-Tyr . . .

3 (SEQ ID NO:20) . . . Ile-Phe-Gln-Ile-Asp-Pro-Met-Leu-Ser-Thr-Tyr-Lys-Tyr . . .

The BE gene construct may require the presence of an amyloplast transit peptide to ensure its correct localisation in the amyloplast, as discussed previously for the glycogen synthase gene. The genes for any such branching enzyme protein may be used in constructs according to this invention.

2C Use of Granule-bound Starch Synthase

The use of cDNA clones of plant granule-bound (waxy) starch synthases are described in U.S. Pat. No. 948,280 and International patent application publication number GB92/0188 1. The amino acid sequences of pea soluble starch synthase isoforms I and II were published by Dry et al (1991, Plant Journal, 2:193–202). Dry et al later described the characterization and sequence of cDNAs encoding two isoforms of granule bound starch synthase from pea and potato (1992, The Plant Journal, 2(2)). Visser et al described the molecular cloning and partial characterization of the gene for granule-bound starch synthase from potato (1989, Plant Sci (Shannon), 64(2):185–192). Visser et al have also decribed the inhibition of the expression of the gene for granule-bound starch synthase in potato by antisense constructs (1991, Mol Gen Genetic, 225(2):289–296).

The following segments of plant starch synthase (and *E coli* glycogen synthase) sequences include the sequence KTGGL (SEQ ID NO:21) which is known to be the ADPG binding site:

SEQ ID NO:22 Pea GEKPPPLAGTNVMNIILVSAECAPWSK-
TGGLGDVAGSLPKAL

SEQ ID NO:23 Maize ASAGMNVVFVGAEMAPWSKTGG
LGDVLGGLP

SEQ ID NO:24 Barley ATGSGMNLVFVGAEMAPWSKTG-
GLGDVLGGLP

SEQ ID NO:25 Potato GKGMNLIFVGTEVGPESKTGGLGDV-
LGGLP

SEQ ID NO:26 (E coli) MQVLHVCSEBFPLLKTGGLADVI-
GALP

The genes for any such starch synthase protein may be used in constructs according to this invention.

2D Use of Soluble Starch Synthase

The use of cDNA clones of plant soluble larch synthases are described in U.S. Pat. No. 948,280 and International patent application publication number GB92/01881. The amino acid sequences of pea soluble starch synthase isoforms I and II were published by Dry et al (1991, Plant Journal, 2:193–202). The amino acid sequence of rice soluble starch synthase was described by Baba etal (1993, Plant Physiology,). This last sequence (rice SSS) incorrectly cites the N-terminal sequence and hence is misleading. Presumably this is because of some extraction error involving a protease degradation or other inherant instability in the extracted enzyme. The correct N-terminal sequence (starting with AELSR) is present in what they refer to as the transit peptide sequence of the rice SSS.

We have determined the amino-acid sequence and nucleotide sequence of maize soluble starch synthase-I (SSS-I). This is a 76 kDa polypeptide which acounts for about half of the SSS activity expressed during endosperm development.

SEQ ID NO:27 N-terminal AELSREGPAPR

SEQ ID NO:28 Internal-1 KNYANAFYTETHI

SEQ ID NO:29 Internal-2 ELGGYIYGQNDMFV-
VNNDHASLVPVLLAAKYIR

SEQ ID NO:30 Internal-3 EVTTAEGGSGLNELL

Nucleotide sequence of a cDNA clone (SEQ ID NO:31) obtained by oligo probing is as follows:

```
CCGCCCGTGC CCGACGCCGG CCTGGGGGTC CTCGGTCTCG

AACCTGAAGG GATTGCTGAA GGTTCCATCG ATAACACAGT

AGTTGTGGCA AGTGAGCAAG ATTCTGAGAT TGTGGTTGGA

AAGGAGCAAG CTCGAGCTAA AGTAACACAA AACATTGTCT

TTGTAACGGC GAAACGTCTC CNNNNGCAAA GTCTGGGGGT

CTAGGAGATC TTTGTGGTTC ATTGCCAGAA GCTCTTGCTG

CTCGTGGTCA CCGTGTGATG GTTGTAATGC CCAGATATTT

AAATAATACC TCCGATAGAT TAGCAAANCG
```

Another important SSS sequence (SEQ ID NO:32) has been obtained from oligo probing, involving the following sequence from another cDNA clone:

```
CCACGCGTCC GGGTTTGATG CAGTATGCTC GCTCTGTGCT

TGTGATACAC AACATTGCTC ATCAGGGTCG TGGCCCTGTA
```

```
GACGACTTCG TCAATTTTNA CTTGCCTGAA CACTACATCG

ACCACTTCAA ACTGTATGAC AACATTGGTG GGGATCACAG

CAACGTTTTT GCTGCGGGGC TGAAGACGGC AGACCGGGTG

GTGACCGTTA GCAATGGCTA CATGTGGGAG CTGAAGACTT

CGGAAGGCGG GTGGGGCCTC CACGACATCA TAAACCAGAA

CGACTGGAAG CTGCAGGGCA TCGTGAACGG CATCGACATG

AGCGAGTGGA ACCCCGCTGT NGACGTGCAC CTCCACTCCG

ACGNCTACAC CAACTACACG TTCG
```

The genes for any such SSS protein may be used in constructs according to this invention.

2E Use of ADP Glucose Pyrophosphorylase

The sequences of bacterial ADPG pyrophosphorylases are known, for example the nucleotide sequence of the E coli glg-C gene (Baecker et al, 1983, J Biol Chem, 258:5084–5088; Leung et al, 1986, J Bacteriol, 167(1):82–88), the glg-C gene from S typhimurium LT2 (Leung et al, 1987, J Bacteriol, 169(9):4349–4354). The GenBank/EMBL database also contains sequences for the E coli glgC gene encoding ADP-glucose pyrophosphorylase.

A review has been published on plant ADP-glucose pyrophosphorylase (Kleczkowski et al, 1991, Journal of Biosciences, 46(7–8);605–612). The isolation and characterisation of cDNA clones for ADPG pyrophosphorylase and waxy locus in wheat was described by Ainsworth and London during a Symposium on molecular strategies for crop improvement held at the 19th Annual UCLA (University of California-Los Angeles) Symposia on molecular and cellular biology, Keystone, Colo., USA, Apr. 16–22, 1990 (J CELL BIOCHEM SUPPL 0 (14 PART E):274). The isolation and nucleotide sequences of cDNA clones encoding ADP-glucose pyrophosphorylase polypeptides from wheat leaf and endosperm were described by Olive et al, 1989, Plant Mol Biol, 12(5):525–538). The genomic nucleotide sequence of a wild-type shrunken-2 allele of Zea mays was described by Shaw and Hannah (1992, Plant Physiol, 98:1214–1216).

DNA encoding ADP-glucose pyrophosphorylase is described in U.S. Pat. No. 930,935 and European patent application publication number EPA 368506; E coli harbouring plasmids containing such DNA were deposited at the National Collection of Industrial and Marine Bacteria on Oct. 19, 1988 under the Accesion Numbers NCIB 40065, NCIB 40066, and NCIB 40067. FIG. 2 shows (SEQ ID NOS:2–3) the cDNA sequence of wheat leaf ADP-glucose pyrophosphorylase (clone WL.AGA.1). FIG. 3 shows (SEQ ID NOS:4–5) the cDNA sequence of wheat leaf ADP-glucose pyrophosphorylase (clone WE.AGA.3) FIG. 4 shows (SEQ ID NOS:6–7) the cDNA sequence of wheat endosperm ADP-glucose pyrophosphorylase (clone WE.AGA.7). The genes for any such ADP glucose pyrophosphorylase protein may be used in constructs according to this invention.

2F Use of Sugary Protein

Recently, the sequence for the maize sugary locus was observed by James and Wright using transposon mutagenesis to locate the gene. The gene for any such protein may be used in constructs according to this invention.

2G Use of Self-Glucosylating Protein

The formation of a glycoprotein primer may be a universal feature for the synthesis of polysaccharides such as starch, glycogen, cellulose etc. The priming molecules may be self-glucosylating proteins (SGP), for example glycogenin which acts as a primer for glycogen synthesis in animals or amylogenin which acts as a primer for starch synthesis in plants (Lomako et al, 1988, FASEB J, 2:3097–3103 and 1990, FEBS Lett, 268:8–12 and 1991, FEBS Lett, 279:223–228; Cao et al, 1993, J Biol Chem, 268(20): 14687–14693; International patent application number GB93/01821). The gene for any such primer may be used in constructs according to this invention.

The glycogenin protein from rabbit skeletal muscle has been sequenced by Campbell and Cohen (1989, Eur J Biochem, 185:119–125), and a glycogenin cDNA has also been identified (Viskupic et al, 1991, FASEB J, 5(6):A1547 and 1992, J Biol Chem, 267(36):25759–25763). The partial amino acid sequencing of peptide fragments of amylogenin from B73 maize was carried out by Gieowar-Singh, Lamoko and Whelan (1992, FASEB J, 6(4):A1520 and A3382); the amino acid sequences of nine purified tryptic peptides (labelled T1–T9) are shown below:

SEQ ID NO:33 T 1 (P 1)-Y V N A V M T I P K

SEQ ID NO:34 T 2 (P 3)-E G A N F V X G Y P F S L R *

SEQ ID NO:35 T 3 (P 4)-Y X X M W A G W T V K

SEQ ID NO:36 T 4 (P 4)-E G A H T A V S H G L W L N I P D Y D A P T Q L V K P K

SEQ ID NO:37 T 5 (P 5)-L G D A M V T W I E A W D E L N P S T P A A A D G K

SEQ ID NO:38 T 6 (P 6)-L G D A M V T D I E A A D E L N P A G P X X X X K

SEQ ID NO:39 T 7 (P 6)-N L L S P S T P F F F N T L Y D P Y R E G A N F V X G Y P F S L R*

SEQ ID NO:40 T 8 (P 7)-G I F W Q E D I I P F F Q N V T I P K

SEQ ID NO:41 T 9 (P 9)-N L D F L E M W R P F F Q P Y H L I I V Q D G D P T K

* radioglucosylated tryptic peptides

The use of glycogenin and amylogenin DNA sequences is described in International patent application number GB93/01821. A cDNA clone encoding amylogenin from B73 maize was deposited at the American Type Culture Collection, 12301 Parklawn Drive, Rockville, Md. 20852, USA under the terms of the Budapest Treaty on Aug. 19, 1993 under the accession number ATCC, 69389. Partial cDNA sequences corresponding to amylogenin are given below in Tables 1 and 2. (SEQ ID NOS:42 and 43 respectively). The genes for any such amylogenin protein may be used in constructs according to this invention.

TABLE 1

| SEQUENCE (I) | |
| --- | --- |
| TGAACTTGGCCTTTGACCGTGA | GCTCATTGGTCCGGCTATGTAC |
| TTCGGTCTCCTGGGTGATGGTC | AGCCTATTGGTCGCTACGACGA |
| TATGTGGGCTGGGTGGTGTGTC | AAGGTGATCTGTGATCATTTGG |
| GATTGGGAGTGAAGACGGGTCT | TCCCTACATCTACCACAGCAAG |
| GCGAGCAACCCATTTGTGAACC | TGAAGAAGGAGTACAAGGGAAT |
| TTTCTGGCAGGAGGACATCATG | CCTTTCTTCCAGAGTGCAAAGC |
| TCTCGAAAGAAGCTGTGACGGT | TCAACAATGCTACATTGAGCTG |
| TCCAAGATGGTGAAGGAGAAGC | TTAGCGCCATTGATCCTTACTT |
| TGACAAGCTTGCTGATGCTATG | GTGACTTGGATTGACGCTTGGG |
| ATGTGCTTAACCCGGCCACATA AG | |

TABLE 2

| SEQUENCE (II) | |
| --- | --- |
| CTTCCGTTCTTCTTTAACACCT | TGTACGATCCCTACCGTGAAGG |
| TGCTGACTTCGTCCGTGGATAC | CCTTTCAGTCTCCGTGAGGGTG |
| TTTCCACTGCTGTTTCTCACGG | TCTCGGGCTCAACATCCCTGAT |
| TACGACGCCCCAACTCAACTCG | TCAAGCCTAAGGAAAGAAACAC |
| AAGGTATGTGGATGCTGTCATG | ACCATCCCAAAGGAACACCTTT |
| GGCCAATTGTGTGGCATGAACT GCC | |

What is claimed is:

1. A food product for human or animal consumption comprising starch extracted from grain comprising starch genes, each of which encodes an enzyme involved in the starch biosynthetic pathway, wherein the endosperm of said grain has a triploid genotype comprising a recessive mutant allele for at least two of said starch genes, and each recessive mutant allele present in any of said starch genes in said triploid genotype is present in one or two doses in said triploid genotype.

2. The food product of claim 1 wherein each recessive mutant allele is an allele of a gene that encodes for a protein selected from group consisting of ADP glucose pyrophosphorylase, debranching enzyme, soluble starch synthase, granule bound starch synthase and branching enzyme.

3. The food product of claim 2 wherein at least one recessive mutant allele is an allele for a gene that encodes granule bound starch synthase.

4. The food product of claim 2 wherein at least one recessive mutant allele is an allele for a gene that encodes branching enzyme.

5. The food product of claim 2 wherein at least one recessive mutant allele is an allele for a gene that encodes soluble starch synthase.

6. A food product for human or animal consumption comprising a starch gel comprising starch extracted from a plant grain having a wild-type triploid endosperm genotype composed of 1 or 2 doses of a recessive mutant allele of a first gene and 1 or 2 doses of a recessive mutant allele of a second gene wherein said first and second genes are independently selected from the group of genes consisting of waxy, amylose extender, dull, horny, sugary, shrunken, brittle, floury and opaque, such that when said first gene and said second gene are not waxy, said wild-type triploid endosperm genotype is not homozygous recessive at the waxy gene.

7. A food product for human or animal consumption comprising a starch gel comprising starch extracted from a plant grain having a wild-type triploid endosperm genotype composed of 1 or 2 doses of a recessive mutant allele of a first gene and 1 or 2 doses of a recessive mutant allele of a second gene and 1 or 2 doses of a recessive mutant allele of a third gene wherein said first and second and third genes are independently selected from the group of genes consisting of waxy, amylose extender, dull, horny, sugary, slinking, brittle, floury and opaque; such that when said first gene, said second gene and said third gene are not waxy, said wild-type triploid endosperm genotype is not homozygous recessive at the waxy gene.

8. The food product of claim 6 wherein said first gene or said second gene is waxy.

9. The food product of claim 7 wherein said first gene or said second gene is waxy.

10. The food product of claim 6 wherein said first gene or said second gene is amylose extender.

11. The food product of claim 7 wherein said first gene or said second gene is amylose extender.

12. The food product of claim 6 wherein said first gene or said second gene is dull.

13. The food product of claim 7 wherein said first gene or said second gene is dull.

14. The food product of claim 6 wherein said first gene or said second gene is horny.

15. The food product of claim 7 wherein said first gene or said second gene is horny.

16. The food product of claim 6 wherein said first gene or said second gene is sugary.

17. The food product of claim 7 wherein said first gene or said second gene is sugary.

18. The food product of claim 6 wherein said first gene or said second gene is shrunken.

19. The food product of claim 7 wherein said first gene or said second gene is shrunken.

20. The food product of claim 6 wherein said first gene or said second gene is brittle.

21. The food product of claim 7 wherein said first gene or said second gene is brittle.

22. The food product of claim 6 wherein said first gene or said second gene is floury.

23. The food product of claim 7 wherein said first gene or said second gene is floury.

24. The food product of claim 6 wherein said first gene or said second gene is opaque.

25. The food product of claim 7 wherein said first gene or said second gene is opaque.

26. The food product of claim 6 wherein said plant is a corn plant.

27. The food product of claim 7 wherein said plant is a corn plant.

28. A food product for human or animal consumption comprising a starch gel according to claim 6, wherein said first and second genes are independently selected from the group consisting of amylose extender, dull, horny, sugary, brittle, floury and opaque.

29. A food product for human or animal consumption comprising a starch gel according to claim 7, wherein said first, second and third genes are independently selected from the group consisting of amylose extender, dull, horny, sugary, brittle, floury and opaque.

30. A food product for human or animal consumption comprising a starch gel according to claim 6, wherein said first and second genes are independently selected from the group consisting of waxy, dull, horny, sugary, shrunken, brittle, floury and opaque.

31. A food product for human or animal consumption comprising a starch gel according to claim 7, wherein said first, second and third genes are independently selected from the group consisting of waxy, dull, horny, sugary, shrunken, brittle, floury and opaque.

32. A food product for human or animal consumption comprising a starch gel according to claim 6, wherein said genotype is composed of 2 doses of said first gene and 2 doses of said second gene.

33. A food product for human or animal consumption comprising a starch gel according to claim 7, wherein said genotype is composed of 2 doses of said first gene and 2 doses of said second gene.

34. A food product for human or animal consumption comprising a starch gel according to claim 28, wherein said genotype is composed of 2 doses of said first gene and 2 doses of said second gene.

35. A food product for human or animal consumption comprising a starch gel according to claim 29, wherein said genotype is composed of 2 doses of said first gene and 2 doses of said second gene.

36. A food product for human or animal consumption comprising a starch gel according to claim 30, wherein said genotype is composed of 2 doses of said first gene and 2 doses of said second gene.

37. A food product for human or animal consumption comprising a starch gel according to claim 31, wherein said genotype is composed of 2 doses of said first gene and 2 doses of said second gene.

38. A food product for human or animal consumption comprising a starch gel according to claim 6, wherein said genotype is composed of 1 dose of said first gene and 2 doses of said second gene.

39. A food product for human or animal consumption comprising a starch gel according to claim 7, wherein said genotype is composed of 1 dose of said first gene and 2 doses of said second gene.

40. A food product for human or animal consumption comprising a starch gel according to claim 28, wherein said genotype is composed of 1 dose of said first gene and 2 doses of said second gene.

41. A food product for human or animal consumption comprising a starch gel according to claim 29, wherein said genotype is composed of 1 dose of said first gene and 2 doses of said second gene.

42. A food product for human or animal consumption comprising a starch gel according to claim 30, wherein said genotype is composed of 1 dose of said first gene and 2 doses of said second gene.

43. A food product for human or animal consumption comprising a starch gel according to claim 31, wherein said genotype is composed of 1 dose of said first gene and 2 doses of said second gene.

* * * * *